United States Patent [19]
Barker et al.

[11] Patent Number: 5,851,775
[45] Date of Patent: Dec. 22, 1998

[54] β-CATENIN, TCF-4, AND APC INTERACT TO PREVENT CANCER

[75] Inventors: Nick Barker, Utrecht; Hans Clevers, Ruysdaellaan, both of Netherlands; Kenneth W. Kinzler, Belair, Md.; Vladimir Korinek, Prague, Czech Rep.; Patrice J. Morin, Columbia, Md.; Andrew B. Sparks; Bert Vogelstein, both of Baltimore, Md.

[73] Assignees: Johns Hopkins University, Baltimore, Md.; Utrecht University, Netherlands

[21] Appl. No.: 821,355

[22] Filed: Mar. 20, 1997

[51] Int. Cl.$^6$ .............................. C12Q 1/68; G01N 33/53
[52] U.S. Cl. ................................ 435/6; 435/7.1; 435/189; 435/366
[58] Field of Search .................................. 435/6, 36, 7.1, 435/189, 366

[56] References Cited

PUBLICATIONS

Curt Suplee, The Washington Post, Key Process In Cancer Is Identified, Finding May Facilitate Early Detection, Therapy, 2–4 (1997).

Bonnee Rubinfeld et al. The Journal of Biological Chemistry, "The APC Protein and E–cadherin Form Similar but Independent Complexes with α–Catenin, β–Catenin, and Plakoglobin", vol. 270, No. 10, pp. 5549–5555 (1995).

J. Kawanishi et al., Molecular and Cellular Biology, "Loss of E–Cadherin–Dependent Cell–Cell Adhesion due to Mutation of the β–Catenin Gene in a Human Cancer Cell Line, HSC–39" vol. 15, No. 3, pp. 1175–1181 (1995).

P.F. Robins, J. Exp. Med., "A Mutated β–Catenin Gene Encodes a Melanoma–specific Antigen Recognized by Tumor Infiltrating Lymphocytes", vol. 183, pp. 1185–1192 (1996).

B. Rubinfeld et al., Science, "Association of the APC Gene Product with β–Catenin", vol. 262, pp. 1731–1734 (1993).

L.K. Su et al., Science, "Association of the APC Tumor Suppressor Protein with Catenins", vol. 262, pp. 1734–1737 (1993).

Bonnee Rubinfeld et al., Science, "Binding of GSK3β to the APC–β–Catenin Complex and Regulation of Complex Assembly", vol. 272, pp 1023–1026 (1996).

Susan Munemitsu et al., Proc. Natl. Acad. Sci., "Regulation of intracellular β–catenin levels by the adenomatous *polyposis coli* (APC) tumor–suppressor protein", vol. 92, pp. 3046–3050 (1995).

Jurgen Behrens et al., Nature, "Functional interaction of βcatenin with the transcription factor LEF–1" vol. 382, pp. 638–642 (1996).

Otmar Huber et al., Mech. Dev., "Nuclear localization of β–catenin by interaction with transcription factor LEF–1", vol. 59, pp. 3–10 (1996).

Miranda Molenaar, Cell, "XTcf–3 Transcription Factor Mediates β–Catenin–Induced Axis Formation in Xenopus Embryos", vol 86, (1996).

*Primary Examiner*—John L. LeGuyader
*Assistant Examiner*—Robert Schwartzman
*Attorney, Agent, or Firm*—Banner & Witcoff, Ltd.

[57] ABSTRACT

The APC tumor suppressor protein binds to β-catenin, a protein recently shown to interact with Tcf/Lef transcription factors. Here, the gene encoding a Tcf family member that is expressed in colonic epithelium (hTcf-4) was cloned and characterized. hTcf-4 transactivates transcription only when associated with β-catenin. Nuclei of APC$^{-/-}$ colon carcinoma cells were found to contain a stable β-catenin-hTCF-4 complex that was constitutively active, as measured by transcription of a Tcf reporter gene. Reintroduction of APC removed β-catenin from hTcf4 and abrogated the transcriptional transactivation. Constitutive transcription of TCF target genes, caused by loss of APC function, may be a crucial event in the early transformation of colonic epithelium. It is also shown here that the products of mutant APC genes found in colorectal tumors are defective in regulating β-catenin/Tcf-4 transcrpitional activation. Furthermore, colorectal tumors with intact APC genes were shown to contain subtle activating mutations of β-catenin that altered functionally significant phosphorylation sites. These results indicate that regulation of β-catenin is critical to APC's tumor suppressive effect and that this regulation can be circumvented by mutations in either APC or β-catenin.

9 Claims, 13 Drawing Sheets

FIG. 1A

```
hTCF-4E    1  - M P Q L N G G G G D D L G A N D E L I S F K D E G E Q E E K - - E S S E
hTCF-1E    1  M M P Q L - D S G G G A G R G D D L G A P D E L L A F Q D E G E E Q D D K N R D S hTCF-4E   34  N S S A E R D L A D V K S S L V N E S E T N Q N S S S D S E A E R R P P R S E
hTCF-1E   41  P V G P E R D L A E L K S S L V N E S E             G A A A G A G V P G P V R V H hTCF-4E   74  S F R D K S R E S L E E A A K R Q D G G L F K G P P Y P G Y P F I M I P D L T S
hTCF-1E   77  G E A E G A P E A L G R E H T S Q R L F P D K     L P E S L E D G L K A P E C T S hTCF-4E  114  P Y L P N G S V S P T A R T Y L Q M K W P L L D V Q A G S L Q S R Q A L K D A R
hTCF-1E  116  G M Y K E T V Y S     A     F N L L M H Y P P P S G A G     Q H P Q                    P hTCF-4E  154  S P S P A H I V S N K V P V V Q P H H Q - P H H P H H P L T P L I T Y S N E H F T P G N P
hTCF-1E  145  Q P - P L H K A N         Q P P H G V P - H - - -           Q L S L Y E H F N S P H P
```

```
470  EGSCLSPPSSDGSLLDSPPPSPNLLGSPPPRDAKSQTEQTQ
427  EGRCPSPVPSDDSAL-GCPGSPAPQDSPSYHLLPRFPPTE

510  MMPPPPALLLAEATHKASALCP
465  LLTSPAEPAPTSPGLSTALSLPTPGPPQAPRSTLQSTQVQ

547  NGALDLPPAALQPAAPSSIAQPSTSWLHSSLAGTQPQ
505  QQESQRQVA*
587  PLSLVTKSLE*
```

```
hTCF-4B  390  LYPGWSARDNYG-KKKKRKRDKQPGETNGEKKSAFATYKVK
hTCF-1B  364  LYPGWSARDNYG-KKKKRRSREKHQESTTGGKRNAFGTYPEK

430  AAASAHPLQMEAY*
         404  AAAPAPFFLPMTVL*
```

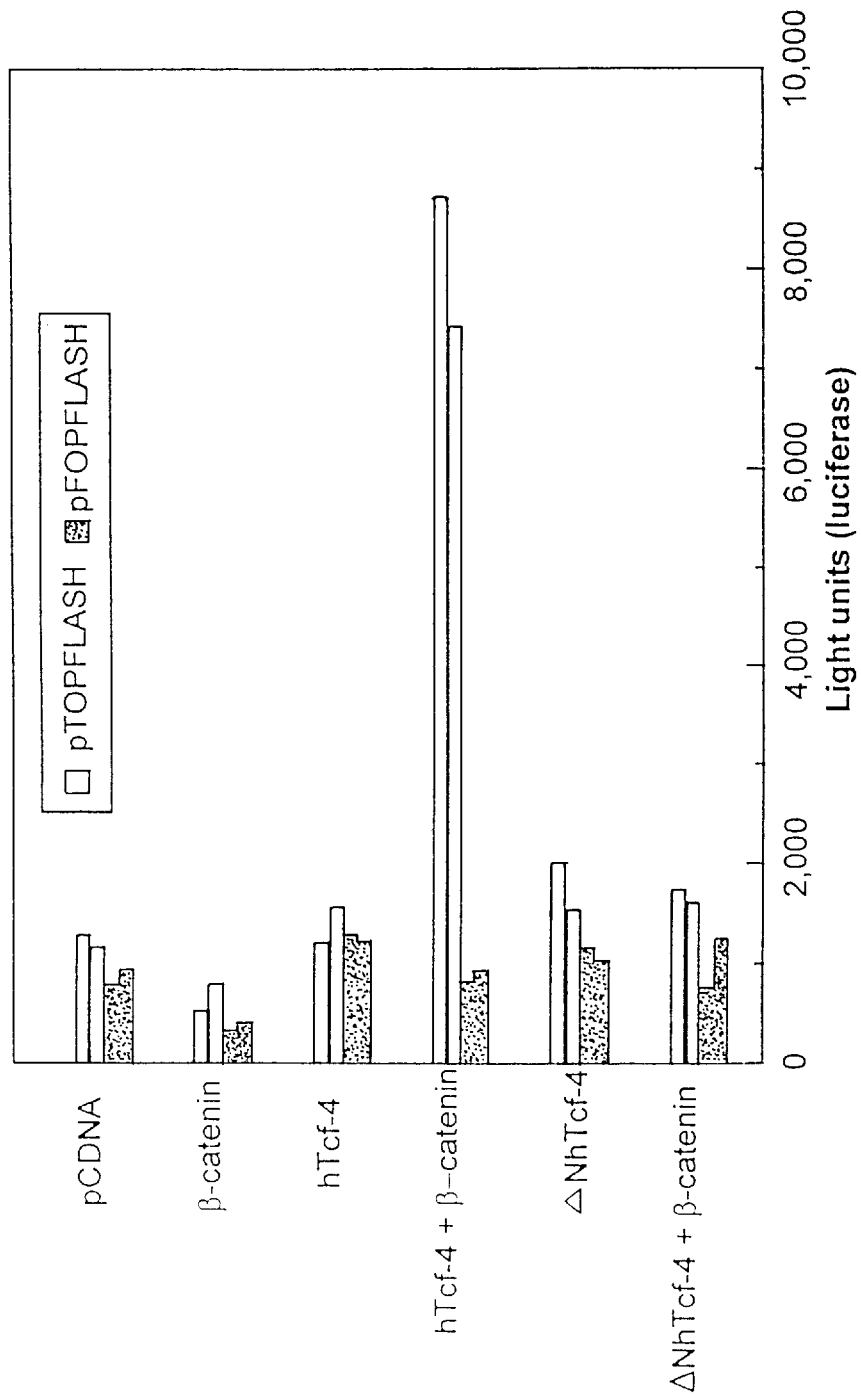

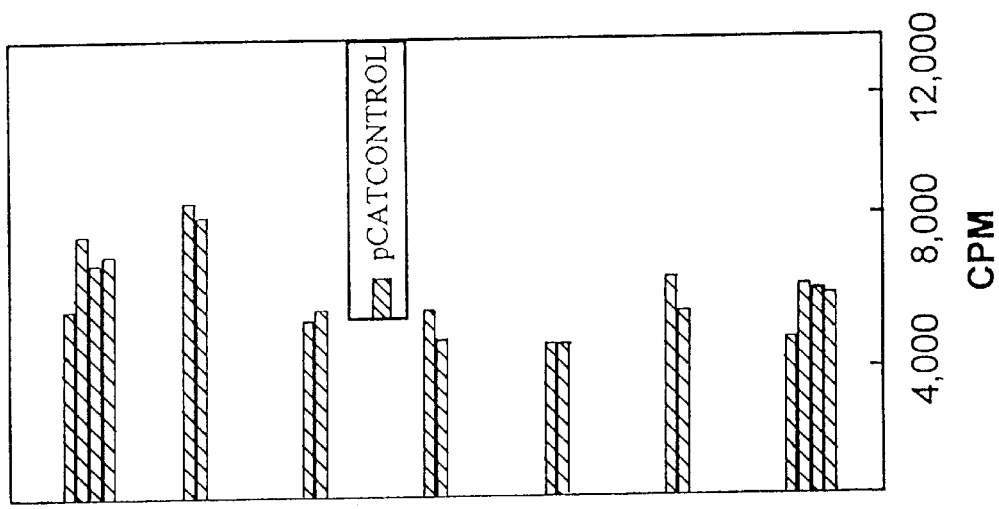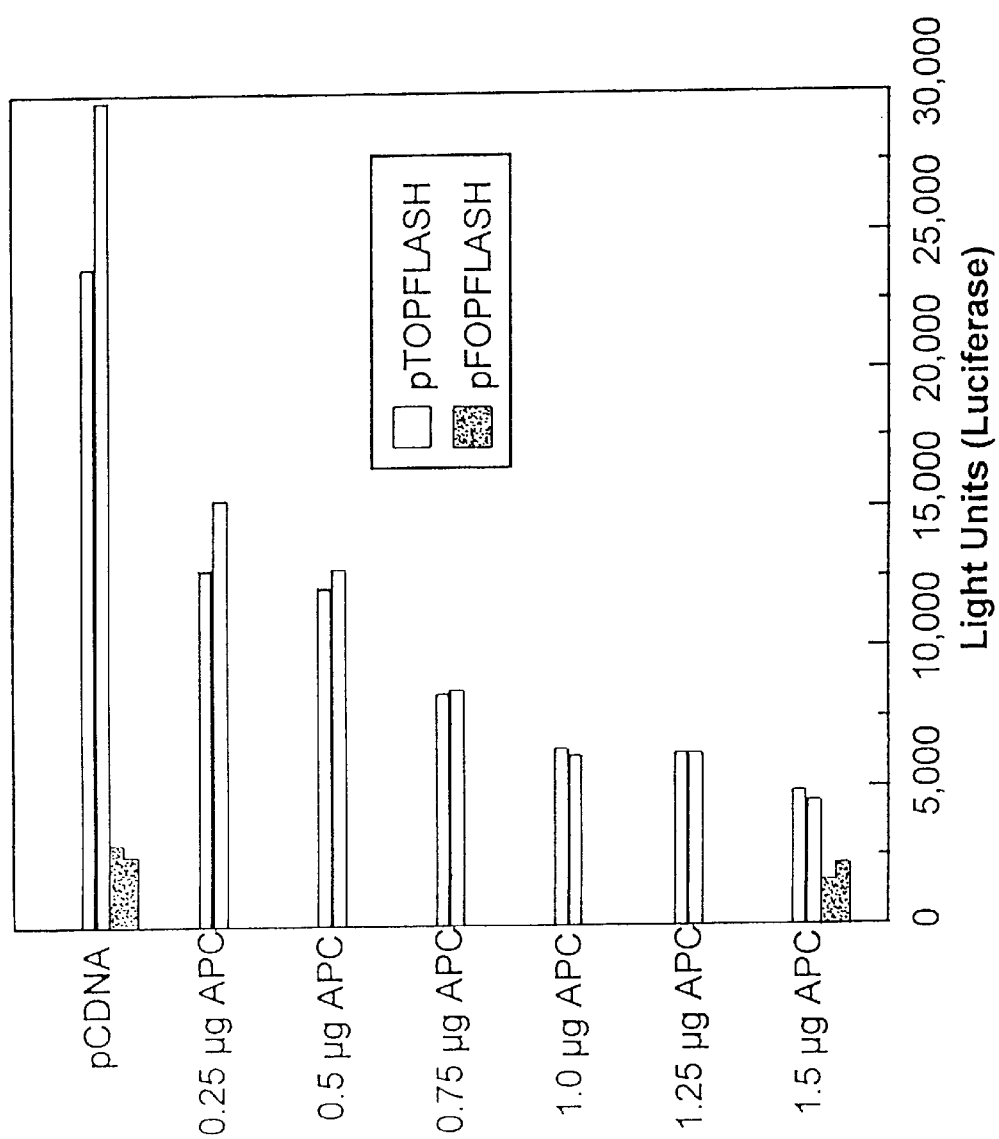

β-CATENIN, TCF-4, AND APC INTERACT TO PREVENT CANCER

The U.S. Government has a paid-up license in this invention and the right in limited circumstances to require the patent owner to license others on reasonable terms as provided for by the terms of grant CA57345 awarded by the National Institutes of Health.

TECHNICAL FIELD OF THE INVENTION

This invention is related to the field of cancer diagnostics and therapeutics. More particularly it relates to methods for diagnosing and treating cancers associated with APC or β-catenin mutations.

BACKGROUND OF THE INVENTION

Mutations of the adenomatous polyposis coli (APC) gene are the most common disease-causing genetic events in humans; approximately 50% of the population will develop colorectal polyps initiated by such mutations during a normal life span (14). Individuals who inherit APC mutations develop thousands of colorectal tumors, consistent with APC's tumor suppressor or "gatekeeping" role in colorectal tumorigenesis (15,16). APC homodimerizes through its amino-terminus (17), and interacts with at least six other proteins: β-catenin (18), γ-catenin (plakoglobin) (19), tubulin (20), EB1 (21), hDLG, a homologue of a Drosophila tumor suppressor protein (22), and ZW3/GSK3β kinase (23). Whether any of these interacting proteins communicate APC growth-controlling signals is unknown. Thus there is a need in the art for a fuller understanding of how the tumor suppressor gene APC functions in cells.

SUMMARY OF THE INVENTION

It is an object of the present invention to provide human nucleotide sequences encoding transcriptional activation proteins.

It is another object of the present invention to provide isolated preparations of transcriptional activation proteins.

It is an object of the present invention to provide methods of determining the presence or absence in a cell of wild-type APC or a downstream protein in the APC transcription regulatory pathway.

Another object of the invention is to provide methods of identifying candidate drugs for use in Familial Adenomatous Polyposis (FAP) patients or patients with increased risk of developing cancer.

It is yet another object of the invention to provide methods of identifying candidate drugs for the treatment of cancer patients, in particular those with APC or β-catenin mutations.

Another object of the invention is to provide a method for diagnosing cancer in a sample suspected of being neoplastic.

Another object of the invention is to provide a method for treating a patient with colorectal cancer or other cancer associated with FAP.

These and other objects of the invention are achieved by providing one or more of the embodiments described below. In one embodiment of the invention an intron-free DNA molecule is provided which encodes Tcf-4 protein as shown in SEQ ID NO: 5 or 6.

According to another embodiment of the invention an isolated Tcf-4 protein is provided. The protein is substantially free of other human proteins, and has a sequence as shown in SEQ ID NO: 5 or 6.

In another embodiment of the invention a method is provided for determining the presence or absence in a cell of wild-type APC or a downstream protein in the APC transcription regulatory pathway. The method comprises the steps of:

introducing a Tcf-responsive reporter gene into the cell; and measuring transcription of said reporter gene; wherein a cell which supports active transcription of said reporter gene does not have wild-type APC or does not have a wild-type downstream protein in the APC transcription regulatory pathway.

According to yet another embodiment of the invention a method is provided for determining the presence or absence in a cell of wild-type APC. The method comprises the steps of:

contacting a Tcf-responsive reporter gene with a lysate of the cell; and measuring transcription of said reporter gene; wherein a lysate which inhibits said transcription has wild-type APC.

In still another embodiment of the invention a method of identifying candidate drugs is provided. The drugs may be useful for treatment of FAP or other cancer patients or patients with increased risk of developing cancer. The method comprises the steps of:

contacting a cell having no wild-type APC or a mutant p-catenin with a test compound;

measuring transcription of a Tcf-responsive reporter gene, wherein a test compound which inhibits the transcription of the reporter gene is a candidate drug for cancer therapy.

According to yet another aspect of the invention another method is provided for identifying candidate drugs for use in for use in FAP patients, colon cancer patients, patients with mutations in β-catenin or APC, or patients with increased risk of developing cancer. The method, comprises the steps of:

contacting a Tcf-responsive reporter gene with a test compound under conditions in which the reporter gene is transcribed in the absence of the test compound; and measuring transcription of the Tcf-responsive reporter gene; wherein a test compound which inhibits said transcription is a candidate drug for cancer therapy.

According to another aspect of the invention a method is provided for identifying candidate drugs for use in FAP patients or patients with increased risk of developing cancer. The method comprises the steps of:

contacting a test compound with β-catenin and Tcf-4 under conditions in which β-catenin and Tcf-4 bind to each other; and determining whether the test compound inhibits the binding of β-catenin and Tcf-4, a test compound which inhibits the binding being a candidate for cancer therapy or prophylaxis.

According to still another embodiment of the invention a method is provided for diagnosing cancer in a sample suspected of being neoplastic. the method comprises the steps of:

comparing a CTNNB sequence found in the sample to a second CTNNB sequence found in a normal tissue, wherein a difference between the first and second sequence is an indicator of cancer.

According to another aspect of the invention a method is provided for treating a patient with colorectal cancer or other cancer associated with FAP.

The method comprises the step of:

administering to the patient a nucleotide sequence comprising a portion of the APC coding sequence, said portion consisting of the p-catenin binding site.

According to another aspect of the invention a method is provided for treating a patient with colorectal cancer or other cancer associated with FAP. The method comprises the step of:

administering to the patient a polypeptide comprising a portion of the APC coding sequence, said portion consisting of the β-catenin binding site.

The present invention thus provides the art with diagnostic, therapeutic and drug discovery methods especially useful for FAP and other cancers with APC or β-catenin mutations.

BRIEF DESCRIPTION OF THE DRAWINGS

Figure 1B:
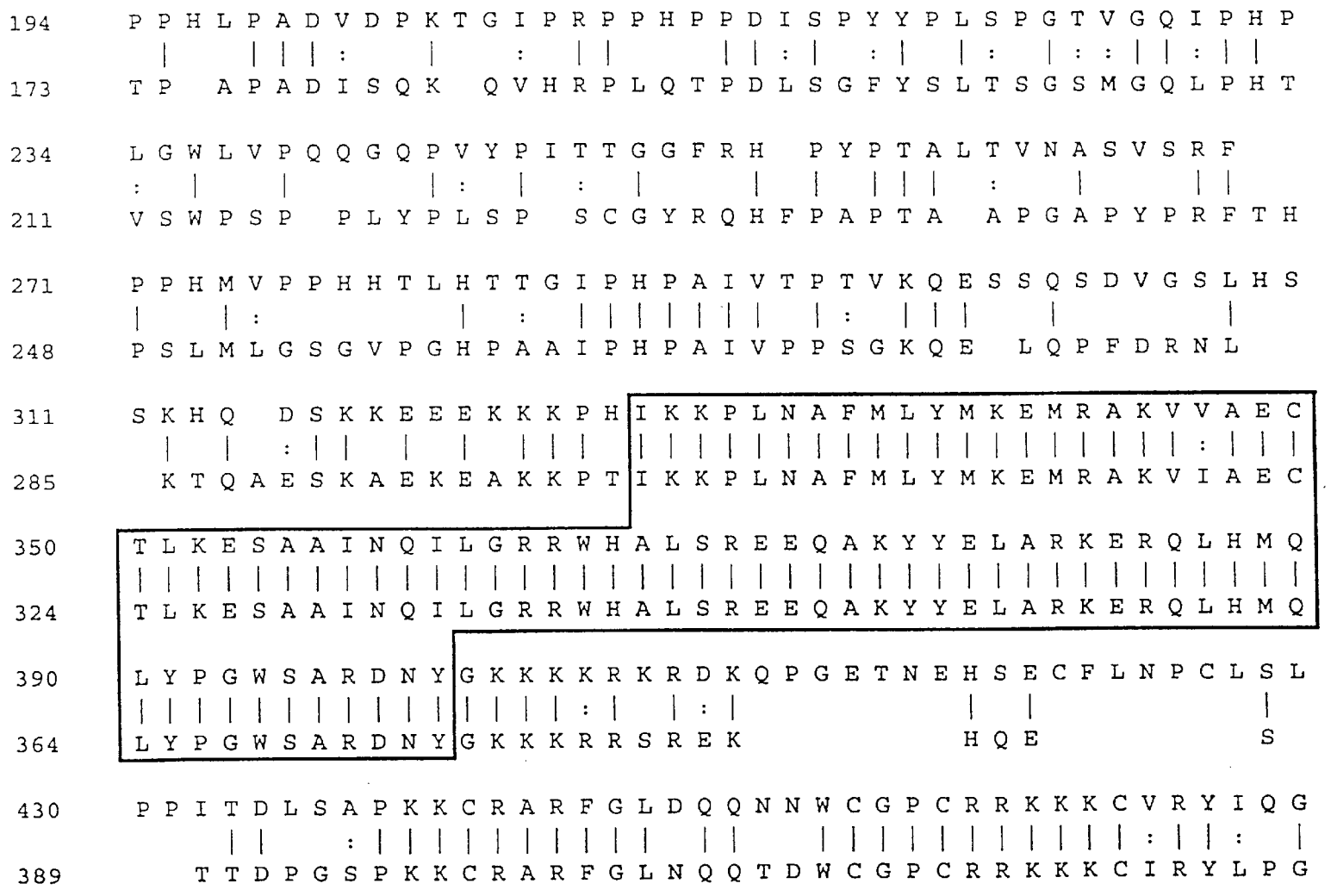

FIG. 1. Sequence comparison of hTcf-4 and hTcf-1.

Two alternative splice forms of hTcf-4 were identified, each encoding a different COOH-terminus. One form (hTcf-4E; SEQ ID NO:6) was homologous to hTCF-IE; SEQ ID NO:9(FIG. 1A) (7); the other form (hTcf-4B; SEQ ID NO:5) was homologous to hTcf-1B; SEQ ID NO:8. (FIG. 1B). The highly conserved $NH_2$-terminal interaction domain and the High Mobility Group (HMG) box DNA-binding region are boxed. Abbreviations for the amino acids are: A. Ala; C, Cys; D, Asp; E, Glu; F, Phe; G, Gly; H, His; I, Ile; IC, Lys; L, Leu; M, Met; N, Asn; P, Pro; Q, Gln; P, Ar g; S, Ser; T, Thr; V, Val; W, Trp; and Y, Tyr.

FIG. 2. Analysis of hTcf-4 expression in colonic epithelium.

(FIG. 2B) In situ hybridization of healthy human colon tissue to an hTcf-4 probe. (FIG. 2C) In situ hybridization to a negative control probe (a fragment of the *E. coli* neomycin resistance gene).

FIGS. 3A, 3B. Transactivational properties of β-catenin/hTcf-4.

All reporter assays were performed as duplicate transfections. For each condition, both values are shown. (FIG. 3A) Reporter gene assays in IIA1.6 B cells. Cells were transfected by electroporation with 1 µg luciferase reporter plasmid, 5 µg β-catenin expression plasmid, and 3 II-hTcf-4 expression plasmids. Empty pCDNA was added to a total of 10 µg, plasmid DNA. (FIG. 3B) Reporter gene assays in SW480 colon carcinoma cells. Cells were transfected with 0.3 µg, of the indicated luciferase reporter gene, 0.7 µg pCATCONTROL as internal control, the indicated amounts of pCMVNeoAPC, and empty PCDNA to a total of 2.5 µg plasmid DNA. Control CAT values are given in the right panel.

(FIG. 5A) Schematics of wild-type (WT) and mutant APC. APC is a 2843-amino-acid (AA) protein (32) with contains armadillo (ARM) repeats in the amino-terminus (33), 15 and 20 AA β-catenin-binding repeats in the central region (18, 19, and a basic region in the carboxyl-terminus (32). The carboxyl-terminus also contains a TXV sequence which mediates DLG binding (22). (FIG. 5B) Effects of WT and mutant APC on CRT. SW480 cells containing endogenous mutant APC were transfected with the APC expression vectors shown in (FIG. 5A) and CRT was measured. Cells were transfected with increasing amounts of WT APC (0, 0.15 and 0.5 µg) or 0.5 µg mutant APC. CRT reporter activities are expressed relative to assays containing no WT APC and are the means of three replicates. Error bars represent standard deviations.

Lipofectamine was used to cotransfect SW480 cells with an internal control (0.5 µg pCMV-βgal), a reporter construct (0.5 µg pTOPFLASH or pFOPFLASH) and the indicated amount of the various APC expression vectors. The pTOPFLASH reporter contained an optimized Tcf-binding site 5' of a luciferase reporter gene, whereas pFOPFLASH contained a mutated site that does not bind Tcf. The amount of DNA in each transfection was kept constant by addition of an appropriate amount of empty expression vector (pCEP4). Luciferase and β-galactosidase activities were determined 16 hours after transfection. Luciferase activity was corrected for transfection efficiency (using the control β-galactosidase activity) and nonspecific transcription (using the pFOPFLASH control).

Figure 5A:
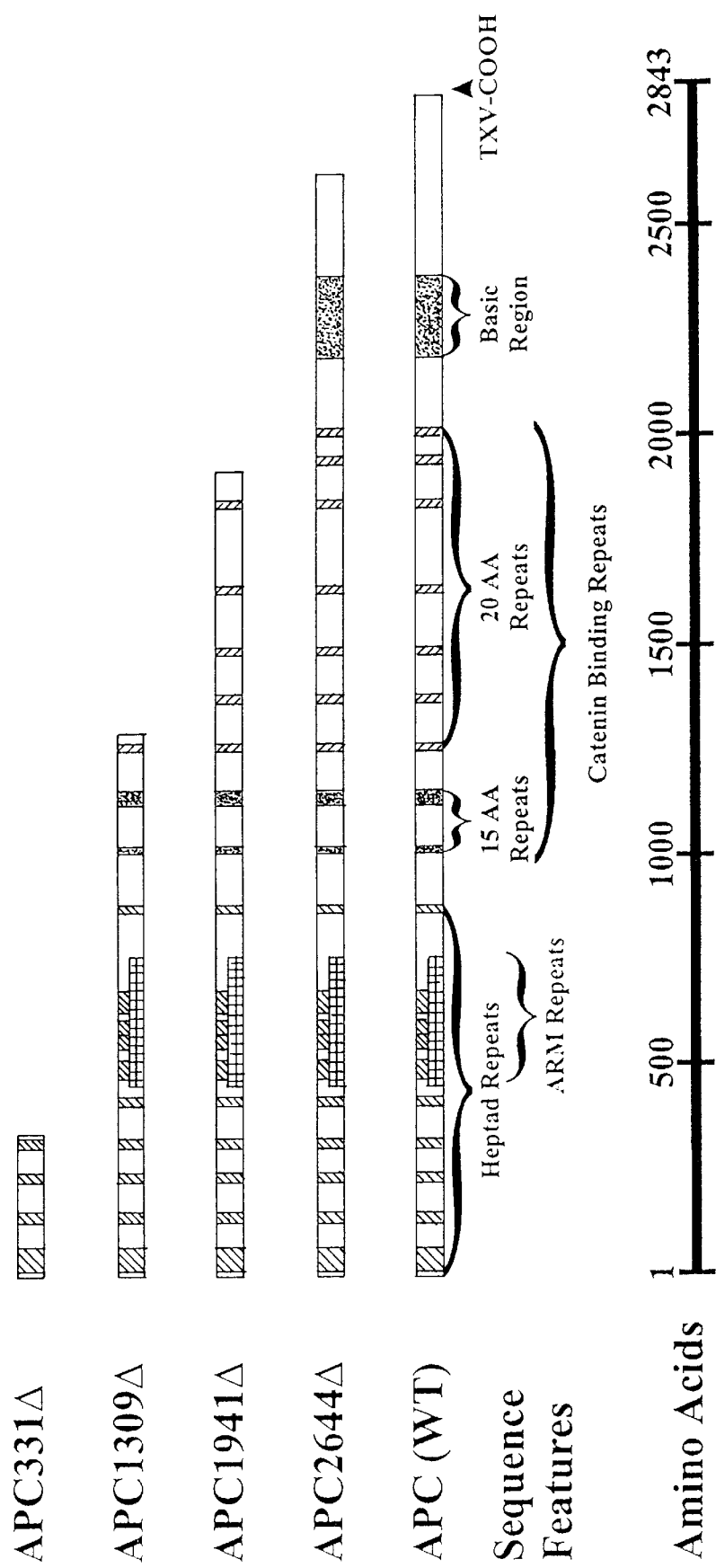
FIGS. 5A and 5B. Effects of APC mutations on CRT.
Figure 5B:
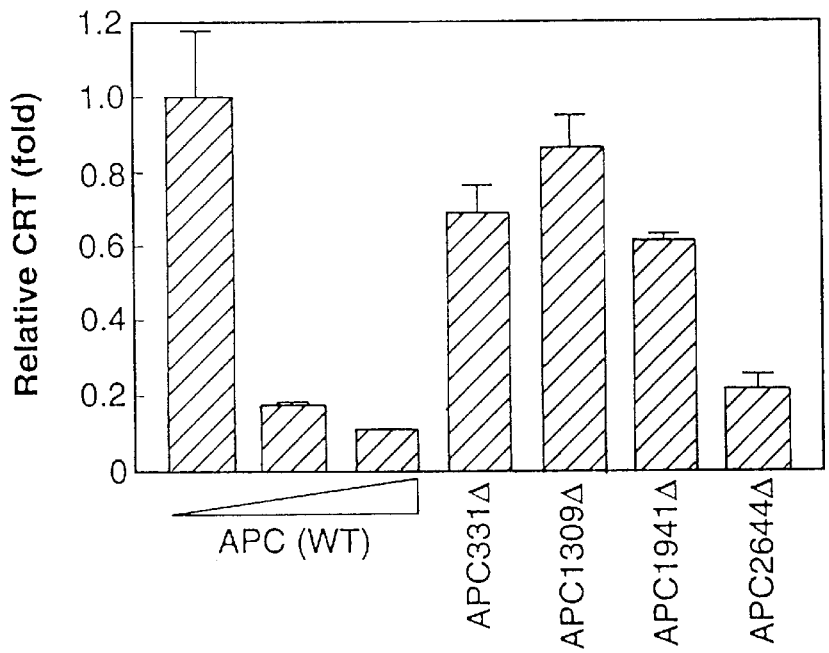
Figure 6B:
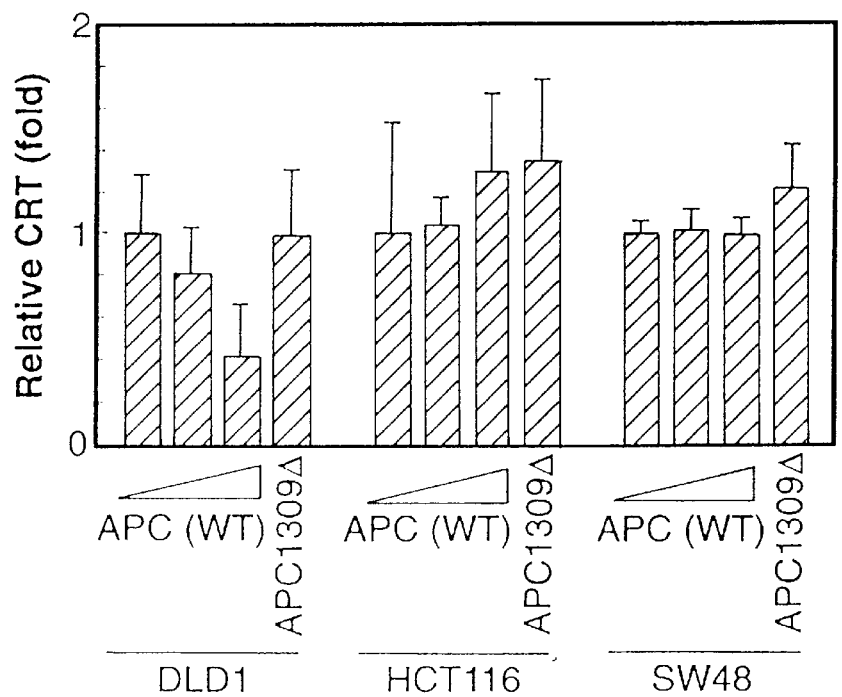
Figure 6A:

FIGS. 6A and 6B. Evaluation of CRT in colorectal cancer cell lines with WT APC. (FIG. 6A) Immunoblot of endogenous APC in the DLD1, SW480, HCT116, SW48 and 293 cell lines, developed with APC monoclonal antibody FE9 (34). (FIG. 6B) Effects of exogenous WT APC on CRT in cell lines with endogenous mutated or WT APC. Cells were transfected with increasing amounts (0, 0.15 µg, 0.5 µg for DLD1 and SW48; 0, 0.5 µg, 5 ,g for HCT116) of WT APC or APC1309Δ mutant (0.5 µg for DLD1 and SW48; 5 µg for HCT116) and CRT was assessed as in FIG. 5. CRT reporter activities are expressed relative to activity in extracts without exogenous APC and are the means of three replicates. Error bars represent standard deviations.

Figure 7A:
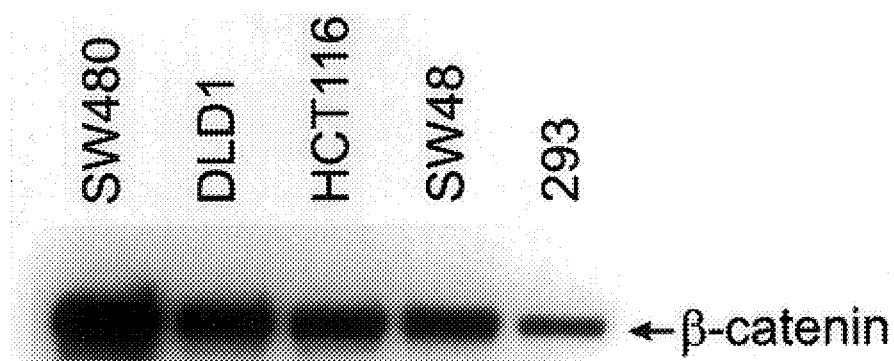
Figure 7B:
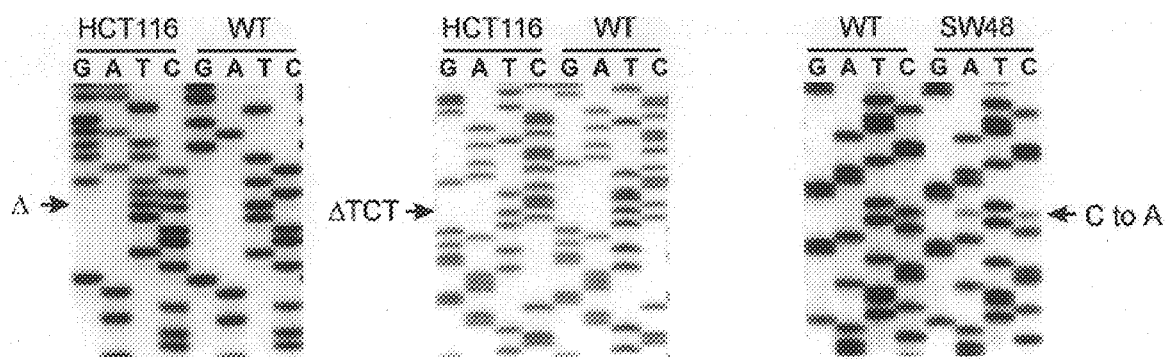
Figure 7C:
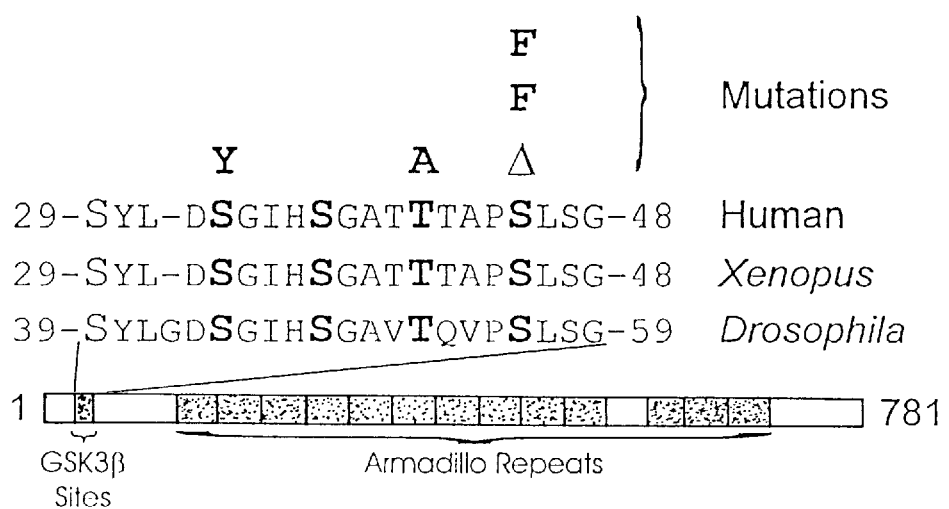

FIGS. 7A, 7B and 7C. Evaluation of β-catenin in colorectal cancer cell lines with WT APC. (FIG. 7A) Immunoblot of the cell lines used in this study, developed with β-catenin monoclonal C19220 (Transduction Laboratories, Lexington, Ky.)(31). (FIG. 7B) Sequence of CTNNB1 in HCT116 and SW48. Overlapping segments constituting the entire CTNNB1 were amplified by RT-PCR from SW480, DLD1, HCT116, and SW48 cells, and sequenced directly with ThermoSequenase (Amersham). In the case of HCT116, a PCR product containing the deleted region was also cloned into pCI-neo (Promega, Madison) and multiple clones corresponding to each allele were individually sequenced.

The left panel (nts 121 to 143 from HCT116) reveals the presence of a deletion in addition to the WT sequence. The middle panel (antisense strand 156 to 113 of the WT and deleted alleles of HCT116) reveals the 3-bp deletion (ΔTCT) that removed codon 45 in half the clones. The right panel (nts 80 to 113 from SW48) reveals a C to A transition affecting codon 33 (TCT to TAT). FIG. 7C) Schematic of β-catenin illustrating the armadillo repeats (33) in human (SEQ ID NO:10), Xenopus (SEQ ID NO:10) and drosophile (SEQ ID NO:11) and negative regulatory domain. The residues in larger type fit the consensus sequence for GSK3β phosphorylation (29) and those in bold have been demonstrated to affect down regulation of β-catenin through GSK3β phosphorylation in Xenopus embryos (27). The five mutations found in human colon cancers are indicated at the top.

Figure 8A:
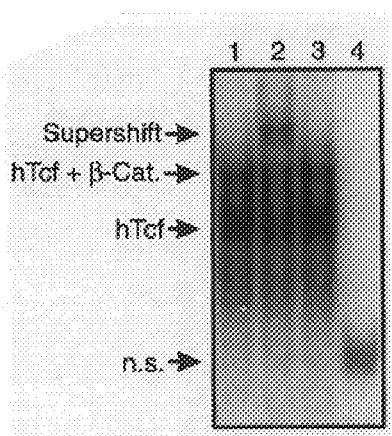

FIGS. 8A and B. Functional evaluation of β-catenin mutants. (FIG. 8A) Constitutive nuclear complex of β-catenin and Tcf in HCT116 cells. The presence of nuclear β-catenin-Tcf complexes was assessed by gel shift assays. Lanes 1 to 3, optimal Tcf retardation probe shifted with nuclear extract from HCT116 cells with addition of no antibody (lane 1), anti β-catenin (0.25 μg, lane 2), or an irrelevant antibody (0.25 μg, lane 3). Lane 4, mutant Tcf retardation probe shifted with nuclear extract from HCT1116 cells. n.s., nonspecific shifting seen with the mutant probe. (FIG. 8B) Effects of the β-catenin mutations on CRT. 293 cells were transfected with WT (WT) or mutant (Δ45, S33Y) β-catenin and CRT was assessed. CRT reporter activities are expressed relative to WT β-catenin and are the means of three replicates. Error bars represent standard deviations. β-catenin expression constructs were prepared as follows. WT CTNNB1 was amplified by RT-PCR from SW480 cells and cloned into the mammalian expression vector pCI-neo (Promega) to produce pCI-neo-β-cat. The pCI-neo-β-cat Δ45 and S33Y were generated by replacing codons 1 to 89 in pCI-neo-β-cat with a PCR product encoding the equivalent region from HCT116 or SW48 cDNA, respectively. The structures of all constructs were verified by sequence analysis. Lipofectamine was used to cotransfect 293 cells with an internal control (0.1 μg CMV-βgal), a reporter (0.5 μg pTOPFLASH or pFOPFLASH), a Tcf-4 expression vector (0.5 μg pCDNA-TCF4), and β-catenin (0.5 μg) or dominant negative hTcf-4 1.0 μg) expression vectors. CRT was determined as described above.

DETAILED DESCRIPTION

It is a discovery of the present invention that hTcf-4 binds to β-catenin and activates transcription in colorectal epithelial cells. Moreover, it has now been found that APC regulates this transcriptional activation, at least in part by binding to β-catenin. In colorectal cancer cells this regulation is frequently abrogated, either by mutation of APC or by mutation of β-catenin.

Two alternative splice forms of human Tcf-4 have been found. One form (hTcf-4E) is homologous to hTcf-1E and the other (hTcf-4B) is homologous to hTcf-1B. The sequence of the nucleotide and amino acid sequences are shown in SEQ ID NOs: 1, 2, 5, and 6. The coding sequences and proteins can be used in assays as described below. Intron-free DNA molecules are provided which are originally made by reverse transcription of a mRNA molecule. They can be propagated in cells or amplified as is desired. Isolated Tcf-4 proteins can be provided substantially free of other human proteins if, for example, the nucleotide sequences are expressed in non-human cells. Methods and vectors for achieving such expression are well known in the art. Choice of such expression means is made by the skilled artisan according to the desired usage and convenience.

Cells can be tested to determine if they have a wild-type APC or a wild-type downstream protein in the APC transcription regulatory pathway, called herein the CRT pathway (β-catenin/Tcf-regulated transcription). One protein within the CRT pathway which has been identified as a target of mutations in human cancers is β-catenin (encoded by the CTNNB1 gene). Other parts of the pathway are also likely to be targets. Although the target genes of the CRT pathway have not been identified, they can be readily identified using the system disclosed here. Genes which are differentially transcribed in the presence of wild-type and mutant CTNNB1, for example, can be identified.

Tcf-responsive reporter genes are those constructs which comprise a readily detectable or assayable gene (such as luciferase, β-galactosidase, chloramphenicol acetyltransferase) linked in cis to a Tcf-responsive element. Such responsive elements are known in the art (7) and any such elements can be used. An optimal Tcf motif contains the sequence CCTTTGATC. From one to twenty copies, and preferably from three to six copies, of the motif may be used. Mutation of the sequence to CCTTTGGCC abrogates responsiveness. Another necessary part of such constructs is a minimal promoter, such as the c-Fos or the Herpes virus thymidine kinase promoter. Transcription of the reporter gene may be performed by any means known in the art, usually by assaying for the activity of the encoded gene, although immunological detection methods can also be used. In addition, transcription can be monitored by measuring the transcribed mRNA directly, typically using oligonucleotide probes.

As shown below, a cell which has a wild-type APC protein will inhibit CRT. However, most mutations in APC render APC unable to inhibit CRT. Similarly, certain mutations in CTNNB1 render β-catenin super-active and/or refractory to the inhibition by APC. Thus measuring Tcf-responsive reporter gene transcription is an indication of the status of APC and CTNNB1. Mutations in both of these genes are associated with cancers and therefore provides diagnostic and prognostic information.

Assays for CRT can be accomplished in vitro or in cells. If the assay is to be accomplished in cells, then a Tcf-responsive reporter gene must be introduced into the cell. Any means for introducing genetic material into cells can be used, including but not limited to infection, transfection, electroporation. If the assay is to be performed in vitro then the components for transcription must be present. These include suitable buffers, RNA polymerase, as well as ribonucleotides. If the protein product is to be assayed, then the components for translation must also be present, such as ribosomes, and amino acids.

These assays can also be used to screen compounds for potential as anti-cancer therapeutic agents. Using either the in vitro or cell form of the assay, test compounds can be introduced to determine whether they are able to mimic the effect of wild-type APC or to convert a mutant APC into a form which is able to inhibit CRT or a mutant β-catenin into a form which is regulatable by APC. In addition, compounds can be tested for the ability to inhibit the binding of β-catenin and Tcf-4, thus mimicking the action of APC. Such a test can be conducted in vitro or in vivo, for example using a two hybrid assay.

A means for diagnosis of cancers is the result of the observation that CTNNB1 mutations are found in tumor cells, especially those which have wild-type APC. Such mutations can be found, inter alia, by sequencing either the gene or the protein found in a sample. Functional assays can also be used, such as whether β-catenin binds to APC or Tcf-4, or whether it is capable of mediating CRT. Sequences can be compared to those found in a normal tissue of a human, especially the same human who provided the sample being tested. Suitable tumors for testing include, but are not limited to those which are associated with FAP. Suitable tumors include colorectal cancer, thyroid cancer, brain cancer, medulloblastoma, desmoid tumor, osteoma, breast cancer, and head and neck cancer. Because APC mutations are so frequent, and because it appears that APC mutations do not occur in the same tumors as CTNNB1 mutations, one can prescreen samples for APC mutations before performing a CTNNB1 determination.

The portion of the APC gene which encodes the β-catenin binding site can be used in a gene therapy format. Suitable techniques are known in the art for administering genes to tumors, and any such technique can be used. Suitable expression vectors are also known in the art and it is within the skill of the artisan to select an appropriate one. Upon expression in a tumor cell of the β-catenin binding portion of APC, β-catenin will be bound and titrated away from binding to Tcf-4, thus preventing unregulated expression of the CRT target genes. Similarly, a polypeptide portion of APC containing the β-catenin binding site can be administered to cells to perform a titration of β-catenin. Techniques for such administration to cells is well known in the art. Cells which are treated with either the polynucleotide or the polypeptide can be used to study the interaction between APC and β-catenin, and for developing drugs which interfere with such binding.

The above disclosure generally describes the present invention. A more complete understanding can be obtained by reference to the following specific examples which are provided herein for purposes of illustration only, and are not intended to limit the scope of the invention.

EXAMPLE 1

This example identifies Tcf-4 as the expressed family member in colorectal epithelial cells and provides the complete sequence of the cloned cDNA.

There are four known members of the Tcf/Lef family in mammals: the lymphoid-specific factors Tcf- I and Lef- 1 (7,8), and the less well characterized Tcf-3 and 4(9). We performed a qualitative Reverse Transcriptase-Polymerase Chain Reaction assay for expression of the four Tcf/Lef genes on 43 colon tumor cell lines. While most colon cell lines expressed more than one of the genes, only hTcf-4 mRNA was expressed in essentially all lines.

Figure 2A:
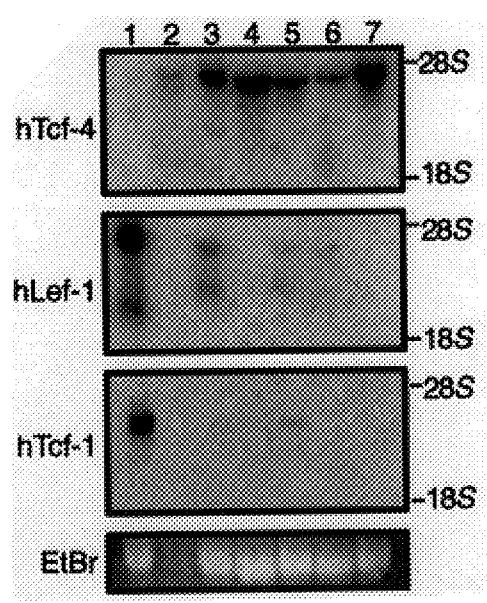
(FIGS. 2A, 2B, and 2C) Northern blot analysis of hTcf-4, hTcf-1, hLef-I expression in Jurkat T cells (lane 1); colonic mucosa (lane 2); colon carcinoma cell lines DLD-1 (lane 3), HCT116 (lane 4); SW480 (lane 5); SW620 (lane 6); HT29 (lane 7). Lane 2 contains 5 µg total RNA; all others contain 15 µg total RNA. The positions of 18S and 28S ribosomal RNAs are shown. EtBr, ethidium bromide stain.

We then screened a human fetal CDNA library and retrieved clones encoding full-length hTcf-4 (FIG. 1). A genomic fragment encoding, the HMG box region of hTcf-4 (7) was used to probe a human 12 week-fetal cDNA library in Lambda GT-11. Positive clones were subcloned into pBluescriptSK and sequenced. See SEQ ID NOs: 1 and 2. The predicted sequence of hTcf-4 was most similar to that of hTcf-1. Alternative splicing yielded two COOH-termini that were conserved between hTcf- I and hTcf-4. The $NH_2$-terminus, which in hTcf- 1, mLef-1 and Xenopus TCF-3 mediates binding to β-catenin (6), was also conserved in hTcf-4. Northern blot analysis of selected colon carcinoma cell lines revealed high-level expression of hTcf-4 (FIG. 2A). Northern blot hybridizations (7) were performed with full-length hTcf-1, hLef-I and hTcf-4 cDNA. Colon epithelial cells were freshly prepared from a mucosal preparation dissected from a healthy surgical colon sample. The sample was minced, and incubated with 1 mM dithiothreitol (DTT) in Hanks' medium to remove mucus. Single-cell suspensions were prepared by incubation at RT in 0.75 mM EDTA in Hanks' medium. Epithelial cells were separated from lymphocytes by Percoll gradient centrifugation.

As evidenced by in situ hybridization (FIG. 2, B and C) and Northern blotting (FIG. 2A), hTcf-4 MRNA was readily detectable in normal colonic epithelium, whereas hTcf-I and hLef-I were not detectable. In situ hybridization of 6μ frozen sections of healthy colon biopsy samples were performed as described(10). hTcf-4 cDNA encoding amino acids 200 to 310 was amplified and labeled with Dig-11-dUTP (Boehringer Mannheim, Germany) by PCR. After hybridization and washing, the sections were sequentially incubated with mouse anti-Dig antibody (Boehringer) and a horseradish peroxidase conjugated rabbit antibody to mouse immunoglobulin (Dako, Glostrup, Denmark). The signal was visualized with diaminobenzidine, which produces a reddish-brown precipitate. Blue counterstining was performed with haematoxyline.

EXAMPLE 2

This example demonstrates the interaction of Tcf-4 and β-catenin and their function as a transcriptional activating factor.

To investigate whether hTcf-4 functionally interacts with β-catenin, we used two sets of reporter constructs in a β-catenin-Tcf reporter gene assay (7). One contained three copies of the optimal Tcf motif CCTTTGATC, or three copies of the mutant motif CCTTTGGCC, upstream of a minimal c-Fos promoter driven-luciferase expression (PTOPFLASH and PFOPFLASH). The second set contained three copies of the optimal motif, or three copies of the mutant motif, upstream of a minimal Herpes virus thymidine kinase promoter driven-Chloramphenicol Acetyl Transferase (CAT) expression (PTOPCAT and PFOPCAT, respectively). Reporter gene assays were performed as in (7). In brief, $2 \times 10^6$ cells were transfected with plasmids by electroporation. After 24 hours, cells were harvested and lysed in 1 mM DTT, 1 % Triton X-100, 15% glycerol, 25 mM Tris pH 7.8 and 8 mM $MgCl_2$. cDNAs encoding Myc-tagged versions of β-catenin and hTcf-4 were inserted into the mammalian expression vector pCDNA (Invitrogen). PCATCONTROL, encoding the CAT enzyme under the control of the SV40 promoter, was purchased from Promega.

Epitope-tagged hTcf-4 and a deletion mutant lacking, the $NH_2$-terminal 30 amino acids (ΔNhTcf-4) were cloned into the expression vector pCDNA. Transient transfections were performed in a murine B cell line (IIA1.6), that does not express any of the Tcf genes (6).

The TOPFLASH reporter was strongly transcribed upon cotransfection with the combination of β-catenin and hTcf-4 plasmids, but not with the individual plasmids or with the combination of β-catenin and ΔNhTcf-4 plasmids. No enhanced transcription was detected in cells transfected with the negative control PFOPFLASH (FIG. 3A). These results show that interaction of the $NH_2$-terminus of hTcf-4 with β-catenin results in transcriptional activation.

EXAMPLE 3

This example demonstrates the functional regulation of CRT transcriptional activation by wild-type APC.

In three APC$^{-/-}$ carcinoma cell lines, SW480, SW620 and DLD-1 (FIG. 3B), the PTOPFLASH reporter was 5–20 fold more actively transcribed than PFOPFLASH. Importantly, transfection of SW480 cells with the reporter gene and an APC-expression vector abrogated the transcriptional activity in a dose-dependent manner (FIG. 3B). In contrast APC had no effect on a cotransfected internal control (pCATCONTROL), or on the basal transcription of PFOPFLASH (FIG. 3B). The use of PTOPCAT and PFOPCAT instead of PTOPFLASH and PFOPFLASH led to comparable observations. The constitutive transcriptional activity of Tcf reporter genes in APC$^{-/-}$ colon carcinoma cells was in stark contrast to the inactivity of these genes in non-colonic cell lines, including IIA1.6 B cells (FIG. 3A), the C57MG breast carcinoma cell line; the Jurkat and BW5147 T cell lines; the Daudi and NS1 B cell lines; the K562 erythromyeloid cell line; the HeLa cervical carcinoma line; the HepG2 hepatoma cell line; 3T3, 3T6, and Rat-I fibroblasts; and the kidney derived SV40-transformed COS cell line (7,16).

EXAMPLE 4

This example demonstrates that a functional β-catenin-hTcf-4 complex exists constitutively in APC$^{-/-}$ cells.

Figure 4:
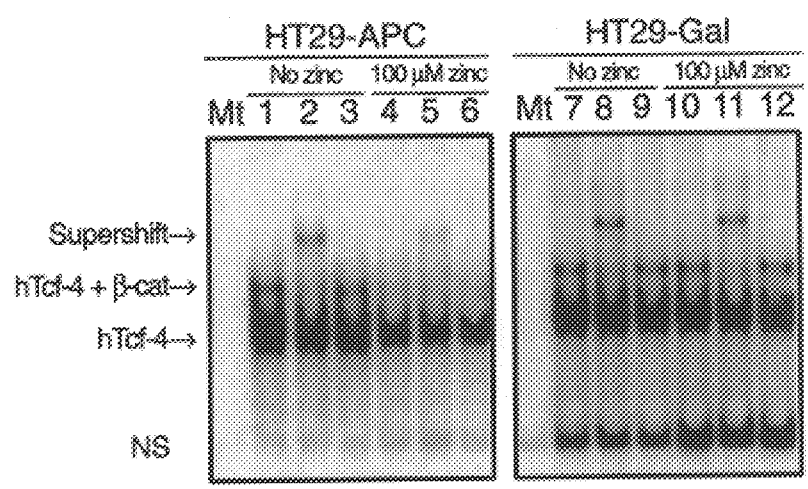
FIG. 4. Constitutive presence of β-catenin-hTcf-4 complexes in APC$^{-/-}$ cells. Gel retardation assays were performed on nuclear extracts from the indicated cell lines before and after a 20-hour exposure to $Zn^{++}$. Samples in lanes 1, 4, 7, 10 were incubated under standard conditions. To the samples in lanes 2, 5, 8, 11, 0.25 µg, anti β-catenin was added. To the samples in lanes 3, 6, 9, 12, 0.25 µg of a control (human CD4) antibody was added. N.S., nonspecific band also observed with mutant (nonbinding) probe (lane Mt).

We used HT29-APC$^{-/-}$ colon carcinoma cells (12), in which APC is controlled by a metallothionein promoter. Induction by Zn$^{++}$ restores wild-type levels of APC, and leads to apoptosis (12). HT29-Gal cells which carry a Zn$^{++}$-inducible LacZ gene were used as a control. The only Tcf family member expressed in HT29 is hTcf-4 (FIG. 2C). In nuclear extracts from uninduced HT29 derived transfectants, we readily detected hTcf-4 by gel retardation (FIG. 4). An additional band of slightly slower mobility was also observed. The addition of a β-catenin antibody resulted in the specific retardation of the latter band, indicating that it represented a β-catenin-hTcf-4 complex (FIG. 4) (12). After Zn$^{++}$ induction for 20 hours, the β-catenin-hTcf-4 complex was diminished sixfold relative to uncomplexed hTcf-4 in HT29-APC1, while no significant change was observed in HT29-Gal cells (FIG. 4). Importantly, the overall levels of cellular β-catenin do not change during the induction period in HT29-APC1 cells (12).

Gel retardation assays were performed as described elsewhere (7). Extracts were prepared from intact nuclei that were washed four times to avoid contamination with cytoplasmic β-catenin. As the optimal Tcf/Lef probe, we used a double-stranded 15-mer CCCTTTGATCTTACC (SEQ ID NO:3); the control probe was CCCTTTGGCCTTACC (SEQ ID NO:4). (All oligonucleotides were from Isogeno, Holland). The β-catenin antibody was purchased from Transduction Laboratories Lexington, Ky.). A typical binding reaction contained 3 μg nuclear protein, 0. 1 ng radiolabeled probe, 100 ng of dIdC, in 25 μl of binding buffer (60 mm KCl, 1 mM EDTA, 1 mM DTT, 10% glycerol). Samples were incubated for 20 min at room temperature, antibody was added, and the samples incubated 20 min further.

On the basis of these data, we propose the following model. In normal colonic epithelium hTcf-4 is the only expressed member of the Tcf family. The interaction of β-catenin with hTcf-4 is regulated by APC. When appropriate extracellular signals are delivered to an epithelial cell, β-catenin accumulates in a form that is not complexed with GSK3β-APC, and that enables its nuclear transport and association with hTcf-4. The HMG domain of hTcf-4 binds in a sequence-specific fashion to the regulatory sequences of specific target genes; β-catenin supplies a transactivation domain. Thus, transcriptional activation of target genes occurs only when hTcf-4 is associated with β-catenin. The hTcf-4 target genes remain to be identified. However, the link with APC and catenin suggests that these genes may participate in the generation and turnover of epithelial cells. Upon loss of wild-type APC, monomeric β-catenin accumulates in the absence of extracellular stimuli, leading to uncontrolled transcription of the hTcf-4 target genes. The apparent de novo expression of other members of the Tcf family in some colon carcinoma cell lines might lead to a further deregulation of Tcf target gene expression by the same mechanism. The control of β-catenin -Tcf signaling is likely to be an important part of the gatekeeper function of APC (19), and its disruption an early step in malignant transformation.

EXAMPLE 5

This example demonstrates that mutant APC protein does not regulate CRT and that a complete set of 20-AA repeats in APC is required to mediate inhibition of CRT.

We tested four APC mutants (FIG. 5A) for their ability to inhibit β-catenin/Tcf-regulated transcription (CRT) in transfection assays. The first mutant, APC331Δ represents a type of mutation found in the germline of Familial Adenomatous Polyposis (FAP) patients as well as in sporadic tumors (15). The APC331Δ protein is truncated at codon 331, amino-terminal to the three 15-amino-acid (AA) β-catenin-binding repeats between codons 1020 and 1169. The second mutant, APC1309Δ, is the most common germline APC mutation (15), a 5-bp deletion that produces a frameshift at codon 1309 and truncation of the protein. The APC1309Δ protein retains the 15-AA β-catenin repeats but lacks the seven 20-AA repeats between codons 1323 and 2075 that have been implicated in binding and phosphorylation of β-catenin (18). The third mutant, APC1941Δ, represents one of the most distal somatic mutations observed in colorectal tumors (25). The APC1941Δ protein is truncated at codon 1941 and therefore contains the 15-AA repeats and all but the last two 20-AA repeats. Finally, APC2644Δ represents a germline mutation resulting from a 4-bp deletion in codon 2644. Patients with this type of unusual carboxyl-terminal mutation develop few polyps (attenuated polyposis) but have pronounced extracolonic disease, particularly desmoid tumors (26).

Each of the APC mutants was cotransfected with a CRT reporter into the SW480 colorectal cancer cell line. SW480 cells have truncated APC and constitutively active CRT which can be suppressed by exogenous WT APC. Although all four mutants produced comparable levels of APC protein after transfection, they varied in their CRT inhibitory activity. The three mutants found in patients with typical polyposis or cancer were markedly deficient in inhibition of CRT (FIG. 5B). The reduced activity of APC1309Δ and APC1941Δ suggests that β-catenin binding is not sufficient for APC-mediated inhibition of CRT and that the complete set of 20-AA repeats is required. Interestingly, the inhibitory activity of the APC2644Δ mutant associated with attenuated polyposis was comparable to that of WT APC (FIG. 5B), suggesting that the DLG-binding domain at the carboxyl-terminus of APC is not required for down-regulation of CRT.

WT and mutant APC constructs (2 μg) were transfected into 293, SW480, and HCT116 cells using Lipofectamine (GIBCO/BRL, Gaithersburg). Protein was harvested 24 hours later and subjected to immunoblot analysis with APC monoclonal antibody FE9 (23). In HCT116 and 293 cells, exogenous WT APC comigrated with the endogenous APC. In SW480 cells, APC1309Δ comigrated with the endogenous mutant APC. In all other cases, the nonfunctional APC constructs (APC331Δ, APC 1309Δ, and APC1941Δ) produced as much or more protein than the CRT-functional forms of APC (APC WT and APC 2644Δ).

EXAMPLE 6

This example demonstrates that other components of the APC-regulatory pathway are affected in some cancer cells.

We evaluated CRT in two colorectal tumor cell lines (HCT116 and SW48) that express full-length APC (FIG. 6A). Both HCT116 and SW48 displayed constitutively active CRT and, in contrast to cell lines with truncated APC (DLD1 and SW480), this activity was not inhibited by exogenous WT APC (FIG. 5B, 6B). Other (noncolorectal cancer) cell lines expressing WT APC do not display constitutive CRT activity. These transfection results suggested that the constitutive CRT in HCT116 and SW48 might be due to an altered downstream component of the APC tumor suppressor pathway.

EXAMPLE 7

This example demonstrates a defect in the gene encoding β-catenin in some cancer cells, which affects CRT.

We evaluated the status of a likely candidate for a downstream component of the APC tumor suppressor pathway, β-catenin, in the same four lines. All four lines expressed similar amounts of apparently intact β-catenin, as assessed by immunoblots (FIG. 7A). However, sequence analysis revealed that both HCT116 and SW48 harbored mutations in the β-catenin gene (CTNNB1) (FIG. 7B). HCT116 had a 3-bp deletion that removed one AA (Ser-45), and SW48 had a C to A missense mutation that changed Ser-33 to Tyr. Analysis of paraffin-embedded archival tissue from the HCT116 patient confirmed the somatic nature of this mutation and its presence in the primary tumor prior to culture. Interestingly, both mutations affected serines that have been implicated in the downregulation of β-catenin through phosphorylation by the ZW3/GSK3β kinase in Xenopus embryos (FIG. 7C) (27,28).

Genomic DNA was isolated from paraffin-embedded normal and tumor tissue from the patient from whom the HCT116 cell line was derived. A 95 bp PCR product encompassing the mutation was then amplified by PCR and directly sequenced using THERMOSEQUENASE (Amersham). The 3 bp deletion was observed in tumor but not in normal tissue.

To test the generality of this mutational mechanism, we evaluated five primary colorectal cancers in which sequencing of the entire coding region of APC revealed no mutations (25). Three of these five tumors were found to contain CTNNB1 mutations (S45F, S45F, and T44A) that altered potential ZW3/GSK3β phosphorylation sites (FIG. 7C). Each mutation appeared to affect only one of the two CTNNB1 alleles and to be somatic.

Genomic DNA was isolated from frozen-sectioned colorectal cancers and a 1001 bp PCR product containing exon 3 of CTNNB1 was then amplified by PCR and directly sequenced using ThermoSequenase (Amersham). An ACC to GCC change at codon 41 (T41A) and a TCT to TTT at codon 45 (S45F) was observed in one and two tumors, respectively.

EXAMPLE 8

This example demonstrates dominant mutations of CTNNB1 that render CRT insensitive to the effects of WT APC.

Figure 8B:
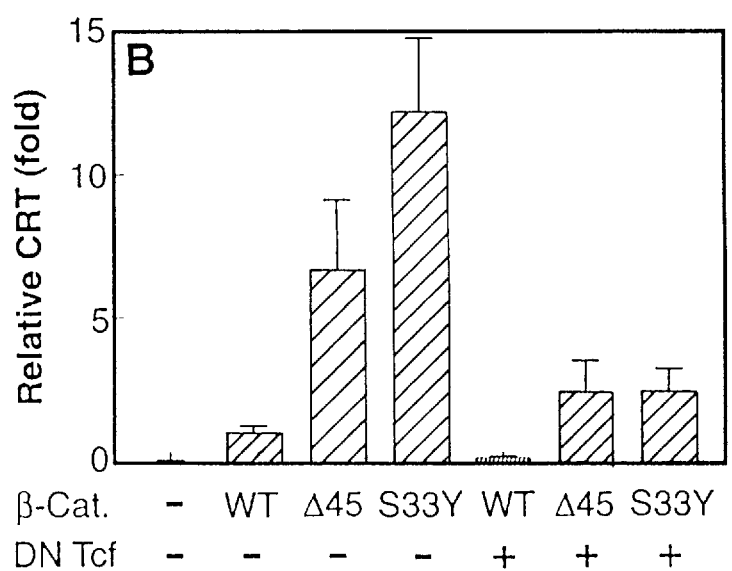

Because the β-catenin mutations were heterozygous, we hypothesized that the mutations might exert a dominant effect, rendering a fraction of cellular β-catenin insensitive to APC-mediated down regulation. To test this notion, we performed gel shift analyses with nuclear extracts from untransfected HCT116 cells. In contrast to noncolorectal cancer cell lines with intact APC, HCT116 cells contained a β-catenin/Tcf complex that gel-shifted an optimized Tcf-binding oligonucleotide, and this complex supershifted with anti-p-catenin (FIG. 8A). We also constructed β-catenin expression vectors and compared the biologic activity of the mutant β-catenin from HCT116 (β-Cat Δ45) and SW48 (β-Cat S33Y) with that of their WT counterpart. For these experiments, we used the 293 kidney epithelial cell line as it is highly transfectable, exhibits low endogenous CRT, and contains a high level of endogenous APC (FIG. 6A). In the presence of endogenous APC, both mutant β-catenins were at least 6-fold more active than the WT protein and this activity was inhibited by dominant-negative hTcf-4 (FIG. 8B).

Together, these results indicate that disruption of APC-mediated regulation of CRT is critical for colorectal tumorigenesis. This is most commonly achieved by recessive inactivating mutations of both APC alleles but, as shown here, can also be achieved by dominant mutations of CTNNB1 that render CRT insensitive to the effects of WT APC. Our results suggest that APC inhibition of CRT requires phosphorylation of β-catenin at multiple sites. These potential phosphorylation sites are consistent with the known specificity of ZW3/β SK3P (29) a serine kinase that negatively regulates β-catenin in Xenopus and Drosophila cells (27) and that interacts with APC and β-catenin in mammalian cells (23). These results also suggest a functional basis for the occasional CTNNB1 mutations observed in other tumor types (30) and illustrate how a critical pathway in human disease can be illuminated by the discovery of mutations in different components of the pathway. The next step in understanding APC function will be the identification of the genes that are activated by hTcf-4/β-catenin complexes and inhibited by WT APC. These genes are likely to be related to APC's ability to induce apoptosis in colorectal cancer cells (31).

REFERENCES

1. B. Rubinfeld et al *Science,* 262, 1731 (1993); L. K. Su, B. Vogelstein, K. W. Kinzler, ibid 262, 1734 (1993).
2. B. Gumbiner, *Curr. Opin. Cell Biol.* 7, 634 (1995).
3. B. Rubinfeld et al, *Science* 272, 1023 (1996).
4. J. Papkoff, B. Rubinfeld, B. Schryver, P. Polakis, *Mol. Cell. BioL* 16, 2128 (1996).
5. S. Munemitsa, B. Souza, I. Albert, B. Rubinfeld, P. Polakis, Proc. *Natl. Acad Sci. U.S.A.* 92, 3046 (1995); B. Rubinfeld, B. Souza, I. Albert, S. Muneinitsa, P. Polakis, *J Biol Chem.* 270, 5549 (1995).
6. M. Molenaar et al, *Cell* 86, 396 (1996); J. Behrens et al, *Nature* 382, 638 (1996); O. Huber et al., *Mech. Dev.* 59, 3 (1996).
7. M. van de Weterinc,, M. Oosterwegel, D. Dooijes, H. Clevers, *EMBO J* 10, 123 (1991); M. van de Wetering, J. Castrop, V. Korinek, Mol Cell Biol, 16, 745 (1996).
8. A. Travis et al. *Genes Dev.* 5, 880 (199 1); M. L. Waterman, W. H. Fischer, K. A. Jones ibid. p. 6562. H. Clevers and R. Grosschedl, *Immunol. Today* 17, 336 (1996).
9. J. Castrop, K. van Norren, H. C. Clevers. *Nucleic Acids Res.* 20, 611 (1992).
10. E. van Hoffen et al, *Am. J Pathol* 149, 1991 (1996).
11. M. van de Wetering, M. Oosterwegel, K. van Norren, H. Clevers, *EMBO J.* 12, 3847 (1993)
12. P. Morin, B. Vogelstein, K. W. Kinzler, *Proc. Natl. Acad. Sci. U.S.A.* 93, 7950 (1996).
13. K. W. Kinzler and B. Vogelstein, *Cell* 87, 159 (1996).
14. About 50% of the Western population develop colorectal adenomas by the age of 70 [D. Ransohoff and C. Lang, *N. Eng.l J. Med.* 325, 37 (1991)] and at least 85% of these tumors contain APC mutations; Y. Miyoshi et al., *Hum Mol Genet* 1, 229–33 (1992); J. Jen et al., *Cancer Res.* 54, 5523 (1994).
15. H. Nagase and Y. Nakamura, *Hum. Mutation* 2, 425 (1993).
16. K. W. Kinzler and B. Vogelstein, *Cell* 87, 159 (1996); S. M. Prescott and R. L. White, ibid., p. 783.
17. G. Joslyn, D. S. Richardson, R. White, T. Alber, *Proc. Natl. Acad. Sci. U.S.A.* 90, 11109 (1993); L. K. Su et al., *Cancer Res.* 53, 2728 (1993).
18. B. Rubinfeld et al., *Science* 262, 1731 (1993); L. K. Su, B. Vogelstein, K. W. Kinzler, ibid., p. 1734.
19. J. Hulsken, J. Behrens, W. Birchmeier, *Curr. Opin. Cell. Biol.* 6, 711 (1994); B. Rubinfeld, B. Souza, I. Albert, S. Munemitsu, P. Polakis, *J. Biol. Chem.* 270, 5549 (1995).
20. S. Munemitsu et al., *Cancer Res.* 54, 3676 (1994); K. J. Smith et al., ibid. p. 3672.
21. L. K. Su et al., *Cancer Res.* 55, 2972 (1995).
22. A. Matsumine et al., *Science* 272, 1020 (1996).
23. B. Rubinfeld et al., *Science* 272, 1023 (1996).
24. M. Molenaar et al., *Cell* 86, 391 (1996); J. Behrens et al., *Nature* 382, 638 (1996).
25. S. M. Powell et al., *Nature* 359, 235 (1992).
26. D. M. Eccles et al., *Am. J. of Hum. Genet.* 59, 1193 (1996); W. Friedl et al., *Hum Genet* 97, 579 (1996); R. J. Scott et al., *Human Molecular Genetics* 5, 1921 (1996).
27. C. Yost et al., *Genes Dev.* 10, 1443 (1996).
28. S. Munemitsu, I. Albert, B. Rubinfeld, P. Polakis, *Mol Cell Biol* 16, 4088 (1996).
29. M. Peifer, L. M. Pai, M. Casey, *Dev. Biol.* 166, 543 (1994).
30. D. J. Kawanishi, et al., *Mol. Cell Biol.* 15, 1175 (1995); P. F. Robbins, et al., *J. Exp. Med.* 183, 1185 (1996).
31. P. J. Morin, B. Vogelstein, K. W. Kinzler, *Proc. Natl. Acad. Sci. U.S.A.* 93, 7950 (1996).
32. J. Groden et al., *Cell* 66, 589 (1991); G. Joslyn et al., ibid., p. 601; K. W. Kinzler et al, *Science* 253, 661 (1991); I. Nishisho et al., ibid., p. 665.
33. M. Peifer, S. Berg, A. B. Reynolds, *Cell* 76, 789 (1994).
34. K. J. Smith et al, *Proc. Natl. Acad. Sci. U.S.A.* 90, 2846 (1993).
35. S. E. Goelz, S. R. Hamilton, B. Vogelstein, *Biochem. Biophys. Res. Commun.* 130, 118 (1985)

We claim:

1. A method of identifying candidate drugs for use in Familial Adenomatous Polyposis (FAP) patients, patients with Adenomatous Polyposis Coli (APC) or β-catenin mutations, or patients with increased risk of developing colorectal cancer, comprising the steps of:

contacting a cell having no wild-type APC or a mutant β-catenin with a test compound, wherein said cell comprises a TCF-responsive reporter gene;

measuring transcription of the Tcf-responsive reporter gene in said cell, wherein a test compound which inhibits the transcription of the reporter gene in said cell is a candidate drug for cancer therapy.

2. The method of claim 1 wherein the cell produces an APC protein defective in β-catenin binding or regulation.

3. The method of claim 1 wherein the cell produces a β-catenin protein which is super-active, or which is defective in APC binding or resistant to APC regulation.

4. The method of claim 1 wherein the cell produces no detectable APC protein.

5. A method of identifying candidate drugs for use in FAP patients, patients with APC or β-catenin mutations, or patients with increased risk of developing colorectal cancer, comprising the steps of:

contacting a Tcf-responsive reporter gene with a test compound under conditions in which the reporter gene is transcribed in the absence of the test compound; and measuring transcription of the Tcf-responsive reporter gene; wherein a test compound which inhibits said transcription is a candidate drug for cancer therapy.

6. The method of claim 5 wherein the step of contacting is performed in the presence of a lysate of a cell which has no wild-type APC.

7. The method of claim 5 wherein the step of contacting is performed in the presence of a lysate of a cell which has a mutant β-catenin defective in APC binding or resistant to APC regulation or which is super-active.

8. The method of claim 6 wherein the cell produces an APC protein defective in β-catenin binding or regulation.

9. A method of identifying candidate drugs for use in PAP patients or patients with increased risk of developing colorectal cancer, comprising the steps of:

contacting a test compound with β-catenin and Tcf-4 under conditions in which β-catenin and Tcf-4 bind to each other; and determining whether the test compound inhibits the binding of β-catenin and Tcf-4, a test compound which inhibits the binding being a candidate for cancer therapy or prophylaxis.

* * * * *

UNITED STATES PATENT AND TRADEMARK OFFICE
CERTIFICATE OF CORRECTION

PATENT NO. : 5,851,775
DATED : December 22, 1998
INVENTOR(S) : Barker et al.

It is certified that error appears in the above-identified patent and that said Letters Patent is hereby corrected as shown below:

Column 3, line 17, change "FIG. 1" to --FIGS. 1A, 1B and 1C--.

Figure 2B:
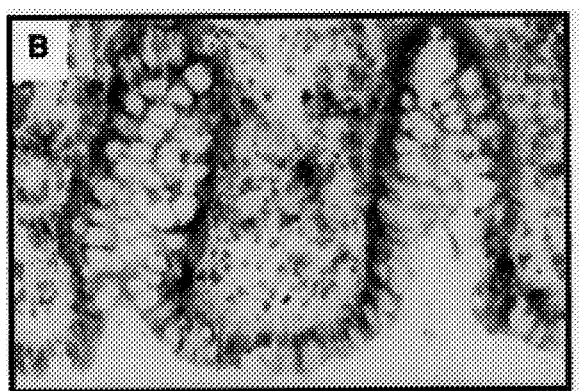
Figure 2C:
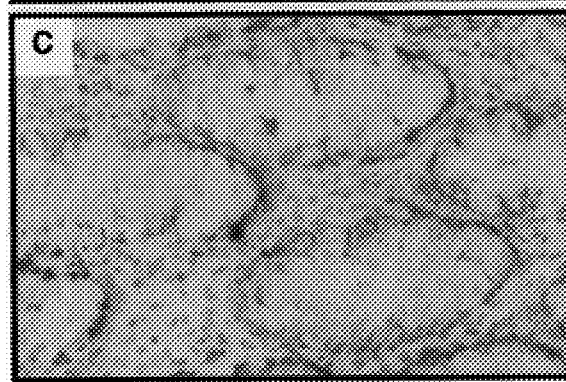

Column 3, line 29, change "FIG. 2" to --FIGS. 2A, 2B and 2C--.

Column 3, line 43, change "FIGS. 3A, 3B" to --FIGS. 3A, 3B and 3C--.

Column 4, line 44, change "FIGS. 7A, 7B and 7C" to --FIGS. 7A and 7B--.

Column 5, line 6, change "B" to --8B--.

Signed and Sealed this

Thirteenth Day of July, 1999

*Attest:*

Q. TODD DICKINSON

*Attesting Officer*  *Acting Commissioner of Patents and Trademarks*

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 2040 base pairs
( B ) TYPE: nucleic acid
( C ) STRANDEDNESS: single
( D ) TOPOLOGY: linear ( x i ) SEQUENCE DESCRIPTION: SEQ ID NO:1:

```
ATGCCGCAGC  TGAACGGCGG  TGGAGGGGAT  GACCTAGGCG  CCAACGACGA  ACTGATTTCC      60
TTCAAAGACG  AGGGCGAACA  GGAGGAGAAG  AGCTCCGAAA  ACTCCTCGGC  AGAGAGGGAT     120
TTAGCTGATG  TCAAATCGTC  TCTAGTCAAT  GAATCAGAAA  CGAATCAAAA  CAGCTCCTCC     180
GATTCCGAGG  CGGAAAGACG  GCCTCCGCCT  CGCTCCGAAA  GTTTCCGAGA  CAAATCCCGG     240
GAAAGTTTGG  AAGAAGCGGC  CAAGAGGCAA  GATGGAGGGC  TCTTTAAGGG  GCCACCGTAT     300
CCCGGCTACC  CCTTCATCAT  GATCCCCGAC  CTGACGAGCC  CCTACCTCCC  CAAGCGATCC     360
GTCTCGCCCA  CCGCCCGAAC  CTATCTCCAG  ATGAAATGGC  CACTGCTTGA  TGTCCAGGCA     420
GGGAGCCTCC  AGAGTAGACA  AGCCCTCAAG  GATGCCCGGT  CCCCATCACC  GGCACACATT     480
GTCTCTAACA  AAGTGCCAGT  GGTGCAGCAC  CCTCACCATG  TCCACCCCT   CACGCCTCTT     540
ATCACGTACA  GCAATGAACA  CTTCACGCCG  GGAAACCCAC  CTCCACACTT  ACCAGCCGAC     600
GTAGACCCCA  AAACAGGAAT  CCCACGGCCT  CCGCACCCTC  CAGATATATC  CCCGTATTAC     660
CCACTATCGC  CTGGCACCGT  AGGACAAATC  CCCCATCCGC  TAGGATGGTT  AGTACCACAG     720
CAAGGTCAAC  CAGTGTACCC  AATCACGACA  GGAGGATTCA  GACACCCCTA  CCCCACAGCT     780
CTGACCGTCA  ATGCTTCCGT  GTCCAGGTTC  CCTCCCATA   TGGTCCCACC  ACATCATACG     840
```

| | | | | | | |
|---|---|---|---|---|---|---|
| CTACACACGA | CGGGCATTCC | GCATCCGGCC | ATAGTCACAC | CAACAGTCAA | ACAGGAATCG | 900 |
| TCCCAGAGTG | ATGTCGGCTC | ACTCCATAGT | TCAAAGCATC | AGGACTCCAA | AAAGGAAGAA | 960 |
| GAAAGAAGA | AGCCCCACAT | AAAGAAACCT | CTTAATGCAT | TCATGTTGTA | TATGAAGGAA | 1020 |
| ATGAGAGCAA | AGGTCGTAGC | TGAGTGCACG | TTGAAAGAAA | GCGCGGCCAT | CAACCAGATC | 1080 |
| CTTGGGCGGA | GGTGGCATGC | ACTGTCCAGA | GAAGAGCAAG | CGAAATACTA | CGAGCTGGCC | 1140 |
| CGGAAGGAGC | GACAGCTTCA | TATGCAACTG | TACCCCGGCT | GGTCCGCGCG | GGATAACTAT | 1200 |
| GGAAGAAGA | AGAAGAGGAA | AAGGGACAAG | CAGCCGGGAG | AGACCAATGG | AGAAAAAAA | 1260 |
| AGTGCGTTCG | CTACATACAA | GGTGAAGGCA | GCTGCCTCAG | CCCACCCTCT | TCAGATGGAA | 1320 |
| GCTTACTAGA | TTCGCCTCCC | CCCTCCCCGA | ACCTGCTAGG | CTCCCCTCCC | CGAGACGCCA | 1380 |
| AGTCACAGAC | TGAGCAGACC | CAGCCTCTGT | CGCTGTCCCT | GAAGCCCGAC | CCCCTGGCCC | 1440 |
| ACCTGTCCAT | GATGCCTCCG | CCACCCGCCC | TCCTGCTCGC | TGAGGCCACC | CACAAGGCCT | 1500 |
| CCGCCCTCTG | TCCCAACGGG | GCCCTGGACC | TGCCCCAGC | CGCTTTGCAG | CCTGCCGCCC | 1560 |
| CCTCCTCATC | AATTGCACAG | CCGTCGACTT | CTTGGTTACA | TTCCCACAGC | TCCCTGGCCG | 1620 |
| GGACCCAGCC | CCAGCCGCTG | TCGCTCGTCA | CCAAGTCTTT | AGAATAGCTT | TAGCGTCGTG | 1680 |
| AACCCCGCTG | CTTTGTTTAT | GGTTTTGTTT | CACTTTTCTT | AATTTGCCCC | CCACCCCCAC | 1740 |
| CTTGAAAGGT | TTTGTTTTGT | ACTCTCTTAA | TTTTGTGCCA | TGTGGCTACA | TTAGTTGATG | 1800 |
| TTTATCGAGT | TCATTGGTCA | ATATTTGACC | CATTCTTATT | TCAATTTCTC | CTTTTAAATA | 1860 |
| TGTAGATGAG | AGAAGAACCT | CATGATTGGT | ACCAAATTT | TTATCAACAG | CTGTTTAAAG | 1920 |
| TCTTTGTAGC | GTTTAAAAAA | TATATATATA | TACATAACTG | TTATGTAGTT | CGGATAGCTT | 1980 |
| AGTTTTAAAA | GACTGATTAA | AAAACAAAAA | AAAAAAAGC | TTGCGAGGGA | TCCCCCGGGA | 2040 |

( 2 ) INFORMATION FOR SEQ ID NO:2:

( i ) SEQUENCE CHARACTERISTICS:
        ( A ) LENGTH: 2444 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

| | | | | | | |
|---|---|---|---|---|---|---|
| GGTTTTTTTT | TTTTACCCCC | CTTTTTTATT | TATTATTTTT | TTGCACATTG | AGCGGATCCT | 60 |
| TGGGAACGAG | AGAAAAAAGA | AACCCAAACT | CACGCGTGCA | GAAGATCTCC | CCCCCCTTCC | 120 |
| CCTCCCCTCC | TCCCTCTTTT | CCCCTCCCCA | GGAGAAAAAG | ACCCCAAGC | AGAAAAAAGT | 180 |
| TCACCTTGGA | CTCGTCTTTT | TCTTGCAATA | TTTTTGGGG | GGGCAAAACT | TTGAGGGGGT | 240 |
| GATTTTTTTT | GGCTTTTCTT | CCTCCTTCAT | TTTTCTTCCA | AAATTGCTGC | TGGTGGGTGA | 300 |
| AAAAAAAATG | CCGCAGCTGA | ACGGCGGTGG | AGGGGATGAC | CTAGGCGCCA | ACGACGAACT | 360 |
| GATTTCCTTC | AAAGACGAGG | GCGAACAGGA | GGAGAAGAGC | TCCGAAAACT | CCTCGGCAGA | 420 |
| GAGGGATTTA | GCTGATGTCA | AATCGTCTCT | AGTCAATGAA | TCAGAAACGA | ATCAAAACAG | 480 |
| CTCCTCCGAT | TCCGAGGCGG | AAAGACGGCC | TCCGCCTCGC | TCCGAAAGTT | CCGAGACAA | 540 |
| ATCCCGGGAA | AGTTTGGAAG | AAGCGGCCAA | GAGGCAAGAT | GGAGGGCTCT | TTAAGGGGCC | 600 |
| ACCGTATCCC | GGCTACCCCT | TCATCATGAT | CCCCGACCTG | ACGAGCCCCT | ACCTCCCCAA | 660 |
| GCGATCCGTC | TCGCCCACCG | CCCGAACCTA | TCTCCAGATG | AAATGGCCAC | TGCTTGATGT | 720 |
| CCAGGCAGGG | AGCCTCCAGA | GTAGACAAGC | CCTCAAGGAT | GCCCGGTCCC | CATCACCGGC | 780 |
| ACACATTGTC | TCTAACAAAG | TGCCAGTGGT | GCAGCACCCT | CACCATGTCC | ACCCCCTCAC | 840 |
| GCCTCTTATC | ACGTACAGCA | ATGAACACTT | CACGCCGGGA | AACCCACCTC | CACACTTACC | 900 |

-continued

| | | | | | |
|---|---|---|---|---|---|
|AGCCGACGTA|GACCCCAAAA|CAGGAATCCC|ACGGCCTCCG|CACCCTCCAG|ATATATCCCC 960|
|GTATTACCCA|CTATCGCCTG|GCACCGTAGG|ACAAATCCCC|CATCCGCTAG|GATGGTTAGT 1020|
|ACCACAGCAA|GGTCAACCAG|TGTACCAAT|CACGACAGGA|GGATTCAGAC|ACCCCTACCC 1080|
|CACAGCTCTG|ACCGTCAATG|CTTCCGTGTC|CAGGTTCCCT|CCCCATATGG|TCCCACCACA 1140|
|TCATACGCTA|CACACGACGG|GCATTCCGCA|TCCGGCCATA|GTCACACCAA|CAGTCAAACA 1200|
|GGAATCGTCC|CAGAGTGATG|TCGGCTCACT|CCATAGTTCA|AAGCATCAGG|ACTCCAAAAA 1260|
|GGAAGAAGAA|AAGAAGAAGC|CCCACATAAA|GAAACCTCTT|AATGCATTCA|TGTTGTATAT 1320|
|GAAGGAAATG|AGAGCAAAGG|TCGTAGCTGA|GTGCACGTTG|AAAGAAAGCG|CGGCCATCAA 1380|
|CCAGATCCTT|GGGCGGAGGT|GGCATGCACT|GTCCAGAGAA|GAGCAAGCGA|AATACTACGA 1440|
|GCTGGCCCGG|AAGGAGCGAC|AGCTTCATAT|GCAACTGTAC|CCCGGCTGGT|CCGCGCGGGA 1500|
|TAACTATGGA|AAGAAGAAGA|AGAGGAAAAG|GGACAAGCAG|CCGGGAGAGA|CCAATGAACA 1560|
|CAGCGAATGT|TTCCTAAATC|CTTGCCTTTC|ACTTCCTCCG|ATTACAGACC|TCAGCGCTCC 1620|
|TAAGAAATGC|CGAGCGCGCT|TTGGCCTTGA|TCAACAGAAT|AACTGGTGCG|GCCCTTGCAG 1680|
|GAGAAAAAAA|AAGTGCGTTC|GCTACATACA|AGGTGAAGGC|AGCTGCCTCA|GCCCACCCTC 1740|
|TTCAGATGGA|AGCTTACTAG|ATTCGCCTCC|CCCCTCCCCG|AACCTGCTAG|GCTCCCCTCC 1800|
|CCGAGACGCC|AAGTCACAGA|CTGAGCAGAC|CCAGCCTCTG|TCGCTGTCCC|TGAAGCCCGA 1860|
|CCCCCTGGCC|CACCTGTCCA|TGATGCCTCC|GCCACCCGCC|CTCCTGCTCG|CTGAGGCCAC 1920|
|CCACAAGGCC|TCCGCCCTCT|GTCCCAACGG|GGCCCTGGAC|CTGCCCCAG|CCGCTTTGCA 1980|
|GCCTGCCGCC|CCCTCCTCAT|CAATTGCACA|GCCGTCGACT|TCTTGGTTAC|ATTCCCACAG 2040|
|CTCCCTGGCC|GGGACCCAGC|CCCAGCCGCT|GTCGCTCGTC|ACCAAGTCTT|TAGAATAGCT 2100|
|TTAGCGTCGT|GAACCCCGCT|GCTTTGTTTA|TGGTTTTGTT|TCACTTTTCT|TAATTTGCCC 2160|
|CCCACCCCCA|CCTTGAAAGG|TTTTGTTTTG|TACTCTCTTA|ATTTTGTGCC|ATGTGGCTAC 2220|
|ATTAGTTGAT|GTTTATCGAG|TTCATTGGTC|AATATTTGAC|CCATTCTTAT|TTCAATTTCT 2280|
|CCTTTTAAAT|ATGTAGATGA|GAGAAGAACC|TCATGATTGG|TACCAAAATT|TTTATCAACA 2340|
|GCTGTTTAAA|GTCTTTGTAG|CGTTTAAAAA|ATATATATAT|ATACATAACT|GTTATGTAGT 2400|
|TCGGATAGCT|TAGTTTTAAA|AGACTGATTA|AAAAACAAAA|AAAA| 2444|

( 2 ) INFORMATION FOR SEQ ID NO:3:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

CCCTTTGATC TTACC        15

( 2 ) INFORMATION FOR SEQ ID NO:4:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

CCCTTTGGCC TTACC        15

(2) INFORMATION FOR SEQ ID NO:5:

(i) SEQUENCE CHARACTERISTICS:
        (A) LENGTH: 442 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:5:

```
Met Pro Gln Leu Asn Gly Gly Gly Asp Asp Leu Gly Ala Asn Asp
 1               5                  10                  15

Glu Leu Ile Ser Phe Lys Asp Glu Gly Glu Gln Glu Glu Lys Ser Ser
                20                  25                  30

Glu Asn Ser Ser Ala Glu Arg Asp Leu Ala Asp Val Lys Ser Ser Leu
            35                  40                  45

Val Asn Glu Ser Glu Thr Asn Gln Asn Ser Ser Ser Asp Ser Glu Ala
        50                  55                  60

Glu Arg Arg Pro Pro Arg Ser Glu Ser Phe Arg Asp Lys Ser Arg
 65                 70                  75                  80

Glu Ser Leu Glu Glu Ala Ala Lys Arg Gln Asp Gly Gly Leu Phe Lys
                85                  90                  95

Gly Pro Pro Tyr Pro Gly Tyr Pro Phe Ile Met Ile Pro Asp Leu Thr
               100                 105                 110

Ser Pro Tyr Leu Pro Lys Arg Ser Val Ser Pro Thr Ala Arg Thr Tyr
           115                 120                 125

Leu Gln Met Lys Trp Pro Leu Leu Asp Val Gln Ala Gly Ser Leu Gln
       130                 135                 140

Ser Arg Gln Ala Leu Lys Asp Ala Arg Ser Pro Ser Pro Ala His Ile
145                 150                 155                 160

Val Ser Asn Lys Val Pro Val Val Gln His Pro His His Val His Pro
               165                 170                 175

Leu Thr Pro Leu Ile Thr Tyr Ser Asn Glu His Phe Thr Pro Gly Asn
           180                 185                 190

Pro Pro Pro His Leu Pro Ala Asp Val Asp Pro Lys Thr Gly Ile Pro
       195                 200                 205

Arg Pro Pro His Pro Pro Asp Ile Ser Pro Tyr Tyr Pro Leu Ser Pro
210                 215                 220

Gly Thr Val Gly Gln Ile Pro His Pro Leu Gly Trp Leu Val Pro Gln
225                 230                 235                 240

Gln Gly Gln Pro Val Tyr Pro Ile Thr Thr Gly Gly Phe Arg His Pro
               245                 250                 255

Tyr Pro Thr Ala Leu Thr Val Asn Ala Ser Val Ser Arg Phe Pro Pro
           260                 265                 270

His Met Val Pro Pro His His Thr Leu His Thr Thr Gly Ile Pro His
       275                 280                 285

Pro Ala Ile Val Thr Pro Thr Val Lys Gln Glu Ser Ser Gln Ser Asp
       290                 295                 300

Val Gly Ser Leu His Ser Ser Lys His Gln Asp Ser Lys Lys Glu Glu
305                 310                 315                 320

Glu Lys Lys Lys Pro His Ile Lys Lys Pro Leu Asn Ala Phe Met Leu
               325                 330                 335

Tyr Met Lys Glu Met Arg Ala Lys Val Val Ala Glu Cys Thr Leu Lys
           340                 345                 350
```

| Glu | Ser | Ala | Ala | Ile | Asn | Gln | Ile | Leu | Gly | Arg | Arg | Trp | His | Ala | Leu |
|---|---|---|---|---|---|---|---|---|---|---|---|---|---|---|---|
| | | 355 | | | | 360 | | | | | | 365 | | | |
| Ser | Arg | Glu | Glu | Gln | Ala | Lys | Tyr | Tyr | Glu | Leu | Ala | Arg | Lys | Glu | Arg |
| | 370 | | | | | 375 | | | | | 380 | | | | |
| Gln | Leu | His | Met | Gln | Leu | Tyr | Pro | Gly | Trp | Ser | Ala | Arg | Asp | Asn | Tyr |
| 385 | | | | | 390 | | | | | 395 | | | | | 400 |
| Gly | Lys | Lys | Lys | Lys | Arg | Lys | Arg | Asp | Lys | Gln | Pro | Gly | Glu | Thr | Asn |
| | | | 405 | | | | | 410 | | | | | 415 | | |
| Gly | Glu | Lys | Lys | Ser | Ala | Phe | Ala | Thr | Tyr | Lys | Val | Lys | Ala | Ala | Ala |
| | | | 420 | | | | | 425 | | | | | 430 | | |
| Ser | Ala | His | Pro | Leu | Gln | Met | Glu | Ala | Tyr | | | | | | |
| | | 435 | | | | | 440 | | | | | | | | |

( 2 ) INFORMATION FOR SEQ ID NO:6:

( i ) SEQUENCE CHARACTERISTICS:
( A ) LENGTH: 596 amino acids
( B ) TYPE: amino acid
( C ) STRANDEDNESS: single
( D ) TOPOLOGY: linear ( i i ) MOLECULE TYPE: None ( x i ) SEQUENCE DESCRIPTION: SEQ ID NO:6:

| Met | Pro | Gln | Leu | Asn | Gly | Gly | Gly | Asp | Asp | Leu | Gly | Ala | Asn | Asp |
|---|---|---|---|---|---|---|---|---|---|---|---|---|---|---|
| 1 | | | | 5 | | | | | 10 | | | | | 15 |
| Glu | Leu | Ile | Ser | Phe | Lys | Asp | Glu | Gly | Glu | Gln | Glu | Glu | Lys | Ser | Ser |
| | | | 20 | | | | | 25 | | | | | 30 | | |
| Glu | Asn | Ser | Ser | Ala | Glu | Arg | Asp | Leu | Ala | Asp | Val | Lys | Ser | Ser | Leu |
| | | | 35 | | | | 40 | | | | | 45 | | | |
| Val | Asn | Glu | Ser | Glu | Thr | Asn | Gln | Asn | Ser | Ser | Ser | Asp | Ser | Glu | Ala |
| | 50 | | | | | 55 | | | | | 60 | | | | |
| Glu | Arg | Arg | Pro | Pro | Arg | Ser | Glu | Ser | Phe | Arg | Asp | Lys | Ser | Arg |
| 65 | | | | | 70 | | | | 75 | | | | | 80 |
| Glu | Ser | Leu | Glu | Glu | Ala | Ala | Lys | Arg | Gln | Asp | Gly | Gly | Leu | Phe | Lys |
| | | | | 85 | | | | | 90 | | | | | 95 | |
| Gly | Pro | Pro | Tyr | Pro | Gly | Tyr | Pro | Phe | Ile | Met | Ile | Pro | Asp | Leu | Thr |
| | | | 100 | | | | | 105 | | | | | 110 | | |
| Ser | Pro | Tyr | Leu | Pro | Asn | Gly | Ser | Val | Ser | Pro | Thr | Ala | Arg | Thr | Tyr |
| | | | 115 | | | | | 120 | | | | | 125 | | |
| Leu | Gln | Met | Lys | Trp | Pro | Leu | Leu | Asp | Val | Gln | Ala | Gly | Ser | Leu | Gln |
| | | | 130 | | | | | 135 | | | | | 140 | | |
| Ser | Arg | Gln | Ala | Leu | Lys | Asp | Ala | Arg | Ser | Pro | Ser | Pro | Ala | His | Ile |
| 145 | | | | | 150 | | | | | 155 | | | | | 160 |
| Val | Ser | Asn | Lys | Val | Pro | Val | Val | Gln | His | Pro | His | His | Val | His | Pro |
| | | | | 165 | | | | | 170 | | | | | 175 | |
| Leu | Thr | Pro | Leu | Ile | Thr | Tyr | Ser | Asn | Glu | His | Phe | Thr | Pro | Gly | Asn |
| | | | 180 | | | | | 185 | | | | | 190 | | |
| Pro | Pro | Pro | His | Leu | Pro | Ala | Asp | Val | Asp | Pro | Lys | Thr | Gly | Ile | Pro |
| | | | 195 | | | | | 200 | | | | | 205 | | |
| Arg | Pro | Pro | His | Pro | Pro | Asp | Ile | Ser | Pro | Tyr | Tyr | Pro | Leu | Ser | Pro |
| | | | 210 | | | | | 215 | | | | | 220 | | |
| Gly | Thr | Val | Gly | Gln | Ile | Pro | His | Pro | Leu | Gly | Trp | Leu | Val | Pro | Gln |
| 225 | | | | | 230 | | | | | 235 | | | | | 240 |
| Gln | Gly | Gln | Pro | Val | Tyr | Pro | Ile | Thr | Thr | Gly | Gly | Phe | Arg | His | Pro |
| | | | | 245 | | | | | 250 | | | | | 255 | |
| Tyr | Pro | Thr | Ala | Leu | Thr | Val | Asn | Ala | Ser | Val | Ser | Arg | Phe | Pro | Pro |

-continued

|     |     |     | 260 |     |     |     | 265 |     |     |     | 270 |     |     |     |
|-----|-----|-----|-----|-----|-----|-----|-----|-----|-----|-----|-----|-----|-----|-----|
| His | Met | Val 275 | Pro | Pro | His | His | Thr 280 | Leu | His | Thr | Thr | Gly 285 | Ile | Pro | His |
| Pro | Ala 290 | Ile | Val | Thr | Pro 295 | Val | Lys | Gln | Glu | Ser 300 | Ser | Gln | Ser | Asp |
| Val 305 | Gly | Ser | Leu | His | Ser 310 | Ser | Lys | His | Gln | Asp 315 | Ser | Lys | Lys | Glu | Glu 320 |
| Glu | Lys | Lys | Lys | Pro 325 | His | Ile | Lys | Lys | Pro 330 | Leu | Asn | Ala | Phe | Met 335 | Leu |
| Tyr | Met | Lys | Glu 340 | Met | Arg | Ala | Lys | Val 345 | Val | Ala | Glu | Cys | Thr 350 | Leu | Lys |
| Glu | Ser | Ala 355 | Ala | Ile | Asn | Gln | Ile 360 | Leu | Gly | Arg | Arg | Trp 365 | His | Ala | Leu |
| Ser | Arg 370 | Glu | Glu | Gln | Ala | Lys 375 | Tyr | Tyr | Glu | Leu | Ala 380 | Arg | Lys | Glu | Arg |
| Gln 385 | Leu | His | Met | Gln | Leu 390 | Tyr | Pro | Gly | Trp | Ser 395 | Ala | Arg | Asp | Asn | Tyr 400 |
| Gly | Lys | Lys | Lys | Lys 405 | Arg | Lys | Arg | Asp | Lys 410 | Gln | Pro | Gly | Glu | Thr | Asn 415 |
| Glu | His | Ser | Glu 420 | Cys | Phe | Leu | Asn | Pro 425 | Cys | Leu | Ser | Leu | Pro 430 | Pro | Ile |
| Thr | Asp | Leu 435 | Ser | Ala | Pro | Lys | Lys 440 | Cys | Arg | Ala | Arg | Phe 445 | Gly | Leu | Asp |
| Gln | Gln 450 | Asn | Asn | Trp | Cys | Gly 455 | Pro | Cys | Arg | Arg | Lys 460 | Lys | Lys | Cys | Val |
| Arg 465 | Tyr | Ile | Gln | Gly | Glu 470 | Gly | Ser | Cys | Leu | Ser 475 | Pro | Pro | Ser | Ser | Asp 480 |
| Gly | Ser | Leu | Leu | Asp 485 | Ser | Pro | Pro | Ser 490 | Pro | Asn | Leu | Leu | Gly 495 | Ser |
| Pro | Pro | Arg | Asp 500 | Ala | Lys | Ser | Gln | Thr 505 | Glu | Gln | Thr | Gln | Pro 510 | Leu | Ser |
| Leu | Ser | Leu 515 | Lys | Pro | Asp | Pro | Leu 520 | Ala | His | Leu | Ser | Met 525 | Met | Pro | Pro |
| Pro | Pro 530 | Ala | Leu | Leu | Leu | Ala 535 | Glu | Ala | Thr | His | Lys 540 | Ala | Ser | Ala | Leu |
| Cys 545 | Pro | Asn | Gly | Ala | Leu 550 | Asp | Leu | Pro | Pro | Ala 555 | Ala | Leu | Gln | Pro | Ala 560 |
| Ala | Pro | Ser | Ser | Ser 565 | Ile | Ala | Gln | Pro | Ser 570 | Thr | Ser | Trp | Leu | His 575 | Ser |
| His | Ser | Ser | Leu 580 | Ala | Gly | Thr | Gln | Pro 585 | Gln | Pro | Leu | Ser | Leu 590 | Val | Thr |
| Lys | Ser | Leu 595 | Glu |

(2) INFORMATION FOR SEQ ID NO:7:

(i) SEQUENCE CHARACTERISTICS:
        (A) LENGTH: 2973 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:7:

| Met 1 | Ala | Ala | Ala | Ser 5 | Tyr | Asp | Gln | Leu | Leu 10 | Lys | Gln | Val | Glu | Ala 15 | Leu |

-continued

| | | | | | | | | | | | | | | |
|---|---|---|---|---|---|---|---|---|---|---|---|---|---|---|
|Lys|Met|Glu|Asn 20|Ser|Asn|Leu|Arg 25|Gln|Glu|Leu|Glu 30|Asp|Ser|Asn|
|His|Leu|Thr 35|Lys|Leu|Glu|Thr 40|Glu|Ala|Ser|Asn|Met 45|Lys|Glu|Val|Leu|
|Lys|Gln 50|Leu|Gln|Gly|Ser 55|Ile|Glu|Asp|Glu|Ala 60|Met|Ala|Ser|Ser|Gly|
|Gln 65|Ile|Asp|Leu|Leu|Glu 70|Arg|Leu|Lys|Glu 75|Leu|Asn|Leu|Asp|Ser|Ser 80|
|Asn|Phe|Pro|Gly|Val 85|Lys|Leu|Arg|Ser|Lys 90|Met|Ser|Leu|Arg|Ser|Tyr 95|
|Gly|Ser|Arg|Glu 100|Gly|Ser|Val|Ser|Ser 105|Arg|Ser|Gly|Glu|Cys 110|Ser|Pro|
|Val|Pro|Met 115|Gly|Ser|Phe|Pro|Arg 120|Arg|Gly|Phe|Val|Asn 125|Gly|Ser|Arg|
|Glu|Ser 130|Thr|Gly|Tyr|Leu|Glu 135|Glu|Leu|Glu|Lys|Glu 140|Arg|Ser|Leu|Leu|
|Leu 145|Ala|Asp|Leu|Asp|Lys 150|Glu|Glu|Lys|Glu 155|Lys|Asp|Trp|Tyr|Tyr|Ala 160|
|Gln|Leu|Gln|Asn|Leu 165|Thr|Lys|Arg|Ile|Asp 170|Ser|Leu|Pro|Leu|Thr 175|Glu|
|Asn|Phe|Ser|Leu 180|Gln|Thr|Asp|Met|Thr 185|Arg|Arg|Gln|Leu|Glu 190|Tyr|Glu|
|Ala|Arg|Gln 195|Ile|Arg|Val|Ala|Met 200|Glu|Glu|Gln|Leu|Gly 205|Thr|Cys|Gln|
|Asp|Met 210|Glu|Lys|Arg|Ala|Gln 215|Arg|Ile|Ala|Arg|Ile 220|Gln|Gln|Ile|
|Glu 225|Lys|Asp|Ile|Leu|Arg 230|Ile|Arg|Gln|Leu|Leu 235|Gln|Ser|Gln|Ala|Thr 240|
|Glu|Ala|Glu|Arg|Ser 245|Ser|Gln|Asn|Lys|His 250|Glu|Thr|Gly|Ser|His 255|Asp|
|Ala|Glu|Arg|Gln 260|Asn|Glu|Gly|Gln|Gly 265|Val|Gly|Glu|Ile|Asn 270|Met|Ala|
|Thr|Ser|Gly 275|Asn|Gly|Gln|Gly|Ser 280|Thr|Thr|Arg|Met|Asp 285|His|Glu|Thr|
|Ala|Ser 290|Val|Leu|Ser|Ser|Ser 295|Ser|Thr|His|Ser|Ala 300|Pro|Arg|Arg|Leu|
|Thr 305|Ser|His|Leu|Gly|Thr 310|Lys|Val|Glu|Met|Val 315|Tyr|Ser|Leu|Leu|Ser 320|
|Met|Leu|Gly|Thr|His 325|Asp|Lys|Asp|Asp|Met 330|Ser|Arg|Thr|Leu|Leu 335|Ala|
|Met|Ser|Ser|Ser 340|Gln|Asp|Ser|Cys|Ile 345|Ser|Met|Arg|Gln|Ser 350|Gly|Cys|
|Leu|Pro|Leu|Leu 355|Ile|Gln|Leu|Leu|His 360|Gly|Asn|Asp|Lys 365|Asp|Ser|Val|
|Leu|Leu|Gly 370|Asn|Ser|Arg|Gly|Ser 375|Lys|Glu|Ala|Arg 380|Ala|Arg|Ala|Ser|
|Ala 385|Ala|Leu|His|Asn|Ile 390|Ile|His|Ser|Gln|Pro 395|Asp|Asp|Lys|Arg|Gly 400|
|Arg|Arg|Glu|Ile|Arg 405|Val|Leu|His|Leu|Leu 410|Glu|Gln|Ile|Arg|Ala 415|Tyr|
|Cys|Glu|Thr|Cys 420|Trp|Glu|Trp|Gln|Glu 425|Ala|His|Glu|Pro|Gly 430|Met|Asp|
|Gln|Asp|Lys|Asn|Pro|Met|Pro|Ala|Pro|Val|Glu|His|Gln|Ile|Cys|Pro|

-continued

```
                      435                                     440                                     445
     Ala  Val  Cys  Val  Leu  Met  Lys  Leu  Ser  Phe  Asp  Glu  His  Arg  His
          450                           455                          460
     Ala  Met  Asn  Glu  Leu  Gly  Gly  Leu  Gln  Ala  Ile  Ala  Glu  Leu  Leu  Gln
     465                      470                           475                           480
     Val  Asp  Cys  Glu  Met  Tyr  Gly  Leu  Thr  Asn  Asp  His  Tyr  Ser  Ile  Thr
                         485                           490                          495
     Leu  Arg  Arg  Tyr  Ala  Gly  Met  Ala  Leu  Thr  Asn  Leu  Thr  Phe  Gly  Asp
                    500                           505                     510
     Val  Ala  Asn  Lys  Ala  Thr  Leu  Cys  Ser  Met  Lys  Gly  Cys  Met  Arg  Ala
                    515                      520                      525
     Leu  Val  Ala  Gln  Leu  Lys  Ser  Glu  Ser  Glu  Asp  Leu  Gln  Gln  Val  Ile
     530                           535                          540
     Ala  Ser  Val  Leu  Arg  Asn  Leu  Ser  Trp  Arg  Ala  Asp  Val  Asn  Ser  Lys
     545                           550                      555                           560
     Lys  Thr  Leu  Arg  Glu  Val  Gly  Ser  Val  Lys  Ala  Leu  Met  Glu  Cys  Ala
                         565                          570                          575
     Leu  Glu  Val  Lys  Lys  Glu  Ser  Thr  Leu  Lys  Ser  Val  Leu  Ser  Ala  Leu
                    580                           585                          590
     Trp  Asn  Leu  Ser  Ala  His  Cys  Thr  Glu  Asn  Lys  Ala  Asp  Ile  Cys  Ala
                    595                      600                      605
     Val  Asp  Gly  Ala  Leu  Ala  Phe  Leu  Val  Gly  Thr  Leu  Thr  Tyr  Arg  Ser
     610                           615                     620
     Gln  Thr  Asn  Thr  Leu  Ala  Ile  Ile  Glu  Ser  Gly  Gly  Ile  Leu  Arg
     625                           630                     635                           640
     Asn  Val  Ser  Ser  Leu  Ile  Ala  Thr  Asn  Glu  Asp  His  Arg  Gln  Ile  Leu
                              645                          650                          655
     Arg  Glu  Asn  Asn  Cys  Leu  Gln  Thr  Leu  Leu  Gln  His  Leu  Lys  Ser  His
                         660                      665                           670
     Ser  Leu  Thr  Ile  Val  Ser  Asn  Ala  Cys  Gly  Thr  Leu  Trp  Asn  Leu  Ser
                    675                      680                      685
     Ala  Arg  Asn  Pro  Lys  Asp  Gln  Glu  Ala  Leu  Trp  Asp  Met  Gly  Ala  Val
     690                           695                     700
     Ser  Met  Leu  Lys  Asn  Leu  Ile  His  Ser  Lys  His  Lys  Met  Ile  Ala  Met
     705                      710                           715                           720
     Gly  Ser  Ala  Ala  Ala  Leu  Arg  Asn  Leu  Met  Ala  Asn  Arg  Pro  Ala  Lys
                         725                           730                          735
     Tyr  Lys  Asp  Ala  Asn  Ile  Met  Ser  Pro  Gly  Ser  Ser  Leu  Pro  Ser  Leu
                         740                      745                     750
     His  Val  Arg  Lys  Gln  Lys  Ala  Leu  Glu  Ala  Glu  Leu  Asp  Ala  Gln  His
                    755                           760                          765
     Leu  Ser  Glu  Thr  Phe  Asp  Asn  Ile  Asp  Asn  Leu  Ser  Pro  Lys  Ala  Ser
          770                           775                          780
     His  Arg  Ser  Lys  Gln  Arg  His  Lys  Gln  Ser  Leu  Tyr  Gly  Asp  Tyr  Val
     785                      790                           795                           800
     Phe  Asp  Thr  Asn  Arg  His  Asp  Asp  Asn  Arg  Ser  Asp  Asn  Phe  Asn  Thr
                         805                           810                          815
     Gly  Asn  Met  Thr  Val  Leu  Ser  Pro  Tyr  Leu  Asn  Thr  Thr  Val  Leu  Pro
                    820                           825                     830
     Ser  Ser  Ser  Ser  Ser  Arg  Gly  Ser  Leu  Asp  Ser  Ser  Arg  Ser  Glu  Lys
                    835                      840                      845
     Asp  Arg  Ser  Leu  Glu  Arg  Glu  Arg  Gly  Ile  Gly  Leu  Gly  Asn  Tyr  His
          850                           855                          860
```

```
Pro Ala Thr Glu Asn Pro Gly Thr Ser Ser Lys Arg Gly Leu Gln Ile
865                 870                 875                 880

Ser Thr Thr Ala Ala Gln Ile Ala Lys Val Met Glu Glu Val Ser Ala
                885                 890                 895

Ile His Thr Ser Gln Glu Asp Arg Ser Gly Ser Thr Thr Glu Leu
            900                 905                 910

His Cys Val Thr Asp Glu Arg Asn Ala Leu Arg Arg Ser Ser Ala Ala
            915                 920                 925

His Thr His Ser Asn Thr Tyr Asn Phe Thr Lys Ser Glu Asn Ser Asn
        930                 935                 940

Arg Thr Cys Ser Met Pro Tyr Ala Lys Leu Glu Tyr Lys Arg Ser Ser
945                 950                 955                 960

Asn Asp Ser Leu Asn Ser Val Ser Ser Asp Gly Tyr Gly Lys Arg
                965                 970                 975

Gly Gln Met Lys Pro Ser Ile Glu Ser Tyr Ser Glu Asp Asp Glu Ser
            980                 985                 990

Lys Phe Cys Ser Tyr Gly Gln Tyr Pro Ala Asp Leu Ala His Lys Ile
        995                 1000                1005

His Ser Ala Asn His Met Asp Asn Asp Gly Glu Leu Asp Thr Pro
    1010                1015                1020

Ile Asn Tyr Ser Leu Lys Tyr Ser Asp Glu Gln Leu Asn Ser Gly Arg
1025                1030                1035                1040

Gln Ser Pro Ser Gln Asn Glu Arg Trp Ala Arg Pro Lys His Ile Ile
                1045                1050                1055

Glu Asp Glu Ile Lys Gln Ser Glu Gln Arg Gln Ser Arg Asn Gln Ser
            1060                1065                1070

Thr Thr Tyr Pro Val Tyr Thr Glu Ser Thr Asp Asp Lys His Leu Lys
            1075                1080                1085

Phe Gln Pro His Phe Gly Gln Gln Glu Cys Val Ser Pro Tyr Arg Ser
    1090                1095                1100

Arg Gly Ala Asn Gly Ser Glu Thr Asn Arg Val Gly Ser Asn His Gly
1105                1110                1115                1120

Ile Asn Gln Asn Val Ser Gln Ser Leu Cys Gln Glu Asp Asp Tyr Glu
                1125                1130                1135

Asp Asp Lys Pro Thr Asn Tyr Ser Glu Arg Tyr Ser Glu Glu Glu Gln
            1140                1145                1150

His Glu Glu Glu Glu Arg Pro Thr Asn Tyr Ser Ile Lys Tyr Asn Glu
        1155                1160                1165

Glu Lys Arg His Val Asp Gln Pro Ile Asp Tyr Ser Leu Lys Tyr Ala
    1170                1175                1180

Thr Asp Ile Pro Ser Ser Gln Lys Gln Ser Phe Ser Phe Ser Lys Ser
1185                1190                1195                1200

Ser Ser Gly Gln Ser Ser Lys Thr Glu His Met Ser Ser Ser Ser Glu
            1205                1210                1215

Asn Thr Ser Thr Pro Ser Ser Asn Ala Lys Arg Gln Asn Gln Leu His
            1220                1225                1230

Pro Ser Ser Ala Gln Ser Arg Ser Gly Gln Pro Gln Lys Ala Ala Thr
            1235                1240                1245

Cys Lys Val Ser Ser Ile Asn Gln Glu Thr Ile Gln Thr Tyr Cys Val
    1250                1255                1260

Glu Asp Thr Pro Ile Cys Phe Ser Arg Cys Ser Ser Leu Ser Ser Leu
1265                1270                1275                1280

Ser Ser Ala Glu Asp Glu Ile Gly Cys Asn Gln Thr Thr Gln Glu Ala
            1285                1290                1295
```

```
Asp  Ser  Ala  Asn  Thr  Leu  Gln  Ile  Ala  Glu  Ile  Lys  Glu  Lys  Ile  Gly
              1300                1305                1310

Thr  Arg  Ser  Ala  Glu  Asp  Pro  Val  Ser  Glu  Val  Pro  Ala  Val  Ser  Gln
              1315                1320                1325

His  Pro  Arg  Thr  Lys  Ser  Ser  Arg  Leu  Gln  Gly  Ser  Ser  Leu  Ser  Ser
              1330                1335                1340

Glu  Ser  Ala  Arg  His  Lys  Ala  Val  Glu  Phe  Ser  Ser  Gly  Ala  Lys  Ser
1345                1350                1355                          1360

Pro  Ser  Lys  Ser  Gly  Ala  Gln  Thr  Pro  Lys  Ser  Pro  Pro  Glu  His  Tyr
              1365                1370                1375

Val  Gln  Glu  Thr  Pro  Leu  Met  Phe  Ser  Arg  Cys  Thr  Ser  Val  Ser  Ser
              1380                1385                1390

Leu  Asp  Ser  Phe  Glu  Ser  Arg  Ser  Ile  Ala  Ser  Ser  Val  Gln  Ser  Glu
              1395                1400                1405

Pro  Cys  Ser  Gly  Met  Val  Ser  Gly  Ile  Ile  Ser  Pro  Ser  Asp  Leu  Pro
              1410                1415                1420

Asp  Ser  Pro  Gly  Gln  Thr  Met  Pro  Pro  Ser  Arg  Ser  Lys  Thr  Pro  Pro
1425                1430                1435                          1440

Pro  Pro  Pro  Gln  Thr  Ala  Gln  Thr  Lys  Arg  Glu  Val  Pro  Lys  Asn  Lys
              1445                1450                1455

Ala  Pro  Thr  Ala  Glu  Lys  Arg  Glu  Ser  Gly  Pro  Lys  Gln  Ala  Val
              1460                1465                1470

Asn  Ala  Ala  Val  Gln  Arg  Val  Gln  Val  Leu  Pro  Asp  Ala  Asp  Thr  Leu
              1475                1480                1485

Leu  His  Phe  Ala  Thr  Glu  Ser  Thr  Pro  Asp  Gly  Phe  Ser  Cys  Ser  Ser
              1490                1495                1500

Ser  Leu  Ser  Ala  Leu  Ser  Leu  Asp  Glu  Pro  Phe  Ile  Gln  Lys  Asp  Val
1505                1510                1515                          1520

Glu  Leu  Arg  Ile  Met  Pro  Pro  Val  Gln  Glu  Asn  Asp  Asn  Gly  Asn  Glu
              1525                1530                1535

Thr  Glu  Ser  Glu  Gln  Pro  Lys  Glu  Ser  Asn  Glu  Asn  Gln  Glu  Lys  Glu
              1540                1545                1550

Ala  Glu  Lys  Thr  Ile  Asp  Ser  Glu  Lys  Asp  Leu  Leu  Asp  Asp  Ser  Asp
              1555                1560                1565

Asp  Asp  Asp  Ile  Glu  Ile  Leu  Glu  Glu  Cys  Ile  Ile  Ser  Ala  Met  Pro
              1570                1575                1580

Thr  Lys  Ser  Ser  Arg  Lys  Ala  Lys  Lys  Pro  Ala  Gln  Thr  Ala  Ser  Lys
1585                1590                1595                          1600

Leu  Pro  Pro  Pro  Val  Ala  Arg  Lys  Pro  Ser  Gln  Leu  Pro  Val  Tyr  Lys
              1605                1610                1615

Leu  Leu  Pro  Ser  Gln  Asn  Arg  Leu  Gln  Pro  Gln  Lys  His  Val  Ser  Phe
              1620                1625                1630

Thr  Pro  Gly  Asp  Asp  Met  Pro  Arg  Val  Tyr  Cys  Val  Glu  Gly  Thr  Pro
              1635                1640                1645

Ile  Asn  Phe  Ser  Thr  Ala  Thr  Ser  Leu  Ser  Asp  Leu  Thr  Ile  Glu  Ser
              1650                1655                1660

Pro  Pro  Asn  Glu  Leu  Ala  Ala  Gly  Glu  Gly  Val  Arg  Gly  Gly  Ala  Gln
1665                1670                1675                          1680

Ser  Gly  Glu  Phe  Glu  Lys  Arg  Asp  Thr  Ile  Pro  Thr  Glu  Gly  Arg  Ser
              1685                1690                1695

Thr  Asp  Glu  Ala  Gln  Gly  Gly  Lys  Thr  Ser  Ser  Val  Thr  Ile  Pro  Glu
              1700                1705                1710

Leu  Asp  Asp  Asn  Lys  Ala  Glu  Glu  Gly  Asp  Ile  Leu  Ala  Glu  Cys  Ile
```

```
                    1715                     1720                     1725
   Asn  Ser  Ala  Met  Pro  Lys  Gly  Lys  Ser  His  Lys  Pro  Phe  Arg  Val  Lys
       1730                     1735                     1740
   Lys  Ile  Met  Asp  Gln  Val  Gln  Gln  Ala  Ser  Ala  Ser  Ser  Ser  Ala  Pro
1745                     1750                     1755                     1760
   Asn  Lys  Asn  Gln  Leu  Asp  Gly  Lys  Lys  Lys  Pro  Thr  Ser  Pro  Val
       1765                     1770                     1775
   Lys  Pro  Ile  Pro  Gln  Asn  Thr  Glu  Tyr  Arg  Thr  Arg  Val  Arg  Lys  Asn
       1780                     1785                     1790
   Ala  Asp  Ser  Lys  Asn  Asn  Leu  Asn  Ala  Glu  Arg  Val  Phe  Ser  Asp  Asn
       1795                     1800                     1805
   Lys  Asp  Ser  Lys  Lys  Gln  Asn  Leu  Lys  Asn  Asn  Ser  Lys  Asp  Phe  Asn
       1810                     1815                     1820
   Asp  Lys  Leu  Pro  Asn  Asn  Glu  Asp  Arg  Val  Arg  Gly  Ser  Phe  Ala  Phe
1825                     1830                     1835                     1840
   Asp  Ser  Pro  His  His  Tyr  Thr  Pro  Ile  Glu  Gly  Thr  Pro  Tyr  Cys  Phe
                    1845                     1850                     1855
   Ser  Arg  Asn  Asp  Ser  Leu  Ser  Ser  Leu  Asp  Phe  Asp  Asp  Asp  Val
       1860                     1865                     1870
   Asp  Leu  Ser  Arg  Glu  Lys  Ala  Glu  Leu  Arg  Lys  Ala  Lys  Glu  Asn  Lys
       1875                     1880                     1885
   Glu  Ser  Glu  Ala  Lys  Val  Thr  Ser  His  Thr  Glu  Leu  Thr  Ser  Asn  Gln
       1890                     1895                     1900
   Gln  Ser  Ala  Asn  Lys  Thr  Gln  Ala  Ile  Ala  Lys  Gln  Pro  Ile  Asn  Arg
1905                     1910                     1915                     1920
   Gly  Gln  Pro  Lys  Pro  Ile  Leu  Gln  Lys  Gln  Ser  Thr  Phe  Pro  Gln  Ser
                    1925                     1930                     1935
   Ser  Lys  Asp  Ile  Pro  Asp  Arg  Gly  Ala  Ala  Thr  Asp  Glu  Lys  Leu  Gln
                    1940                     1945                     1950
   Asn  Phe  Ala  Ile  Glu  Asn  Thr  Pro  Val  Cys  Phe  Ser  His  Asn  Ser  Ser
                    1955                     1960                     1965
   Leu  Ser  Ser  Leu  Ser  Asp  Ile  Asp  Gln  Glu  Asn  Asn  Lys  Glu  Asn
       1970                     1975                     1980
   Glu  Pro  Ile  Lys  Glu  Thr  Glu  Pro  Pro  Asp  Ser  Gln  Gly  Glu  Pro  Ser
1985                     1990                     1995                     2000
   Lys  Pro  Gln  Ala  Ser  Gly  Tyr  Ala  Pro  Lys  Ser  Phe  His  Val  Glu  Asp
                    2005                     2010                     2015
   Thr  Pro  Val  Cys  Phe  Ser  Arg  Asn  Ser  Ser  Leu  Ser  Ser  Leu  Ser  Ile
                    2020                     2025                     2030
   Asp  Ser  Glu  Asp  Asp  Leu  Leu  Gln  Glu  Cys  Ile  Ser  Ser  Ala  Met  Pro
                    2035                     2040                     2045
   Lys  Lys  Lys  Lys  Pro  Ser  Arg  Leu  Lys  Gly  Asp  Asn  Glu  Lys  His  Ser
       2050                     2055                     2060
   Pro  Arg  Asn  Met  Gly  Gly  Ile  Leu  Gly  Glu  Asp  Leu  Thr  Leu  Asp  Leu
2065                     2070                     2075                     2080
   Lys  Asp  Ile  Gln  Arg  Pro  Asp  Ser  Glu  His  Gly  Leu  Ser  Pro  Asp  Ser
                    2085                     2090                     2095
   Glu  Asn  Phe  Asp  Trp  Lys  Ala  Ile  Gln  Glu  Gly  Ala  Asn  Ser  Ile  Val
                    2100                     2105                     2110
   Ser  Ser  Leu  His  Gln  Ala  Ala  Ala  Ala  Ala  Cys  Leu  Ser  Arg  Gln  Ala
       2115                     2120                     2125
   Ser  Ser  Asp  Ser  Asp  Ser  Ile  Leu  Ser  Leu  Lys  Ser  Gly  Ile  Ser  Leu
       2130                     2135                     2140
```

```
Gly Ser Pro Phe His Leu Thr Pro Asp Gln Glu Glu Lys Pro Phe Thr
2145                2150                2155                2160

Ser Asn Lys Gly Pro Arg Ile Leu Lys Pro Gly Glu Lys Ser Thr Leu
                2165                2170                2175

Glu Thr Lys Lys Ile Glu Ser Glu Lys Gly Ile Lys Gly Gly Lys
            2180                2185                2190

Lys Val Tyr Lys Ser Leu Ile Thr Gly Lys Val Arg Ser Asn Ser Glu
            2195                2200                2205

Ile Ser Gly Gln Met Lys Gln Pro Leu Gln Ala Asn Met Pro Ser Ile
            2210                2215                2220

Ser Arg Gly Arg Thr Met Ile His Ile Pro Gly Val Arg Asn Ser Ser
2225                2230                2235                2240

Ser Ser Thr Ser Pro Val Ser Lys Lys Gly Pro Pro Leu Lys Thr Pro
                2245                2250                2255

Ala Ser Lys Ser Pro Ser Glu Gly Gln Thr Ala Thr Thr Ser Pro Arg
                2260                2265                2270

Gly Ala Lys Pro Ser Val Lys Ser Glu Leu Ser Pro Val Ala Arg Gln
            2275                2280                2285

Thr Ser Gln Ile Gly Gly Ser Ser Lys Ala Pro Ser Arg Ser Gly Ser
        2290                2295                2300

Arg Asp Ser Thr Pro Ser Arg Pro Ala Gln Gln Pro Leu Ser Arg Pro
2305                2310                2315                2320

Ile Gln Ser Pro Gly Arg Asn Ser Ile Ser Pro Gly Arg Asn Gly Ile
                2325                2330                2335

Ser Pro Pro Asn Lys Leu Ser Gln Leu Pro Arg Thr Ser Ser Pro Ser
            2340                2345                2350

Thr Ala Ser Thr Lys Ser Ser Gly Ser Gly Lys Met Ser Tyr Thr Ser
        2355                2360                2365

Pro Gly Arg Gln Met Ser Gln Gln Asn Leu Thr Lys Gln Thr Gly Leu
        2370                2375                2380

Ser Lys Asn Ala Ser Ser Ile Pro Arg Ser Glu Ser Ala Ser Lys Gly
2385                2390                2395                2400

Leu Asn Gln Met Asn Asn Gly Asn Gly Ala Asn Lys Lys Val Glu Leu
                2405                2410                2415

Ser Arg Met Ser Ser Thr Lys Ser Ser Gly Ser Glu Ser Asp Arg Ser
            2420                2425                2430

Glu Arg Pro Val Leu Val Arg Gln Ser Thr Phe Ile Lys Glu Ala Pro
            2435                2440                2445

Ser Pro Thr Leu Arg Arg Lys Leu Glu Glu Ser Ala Ser Phe Glu Ser
        2450                2455                2460

Leu Ser Pro Ser Ser Arg Pro Ala Ser Pro Thr Arg Ser Gln Ala Gln
2465                2470                2475                2480

Thr Pro Val Leu Ser Pro Ser Leu Pro Asp Met Ser Leu Ser Thr His
                2485                2490                2495

Ser Ser Val Gln Ala Gly Gly Trp Arg Lys Leu Pro Pro Asn Leu Ser
            2500                2505                2510

Pro Thr Ile Glu Tyr Asn Asp Gly Arg Pro Ala Lys Arg His Asp Ile
        2515                2520                2525

Ala Arg Ser His Ser Glu Ser Pro Ser Arg Leu Pro Ile Asn Arg Ser
        2530                2535                2540

Gly Thr Trp Lys Arg Glu His Ser Lys His Ser Ser Ser Leu Pro Arg
2545                2550                2555                2560

Val Ser Thr Trp Arg Arg Thr Gly Ser Ser Ser Ser Ile Leu Ser Ala
            2565                2570                2575
```

Ser Ser Glu Ser Ser Glu Lys Ala Lys Ser Glu Asp Glu Lys His Val
            2580                    2585                    2590

Asn Ser Ile Ser Gly Thr Lys Gln Ser Lys Glu Asn Gln Val Ser Ala
            2595                    2600                    2605

Lys Gly Thr Trp Arg Lys Ile Lys Glu Asn Glu Phe Ser Pro Thr Asn
            2610                    2615                    2620

Ser Thr Ser Gln Thr Val Ser Ser Gly Ala Thr Asn Gly Ala Glu Ser
2625                    2630                    2635                    2640

Lys Thr Leu Ile Tyr Gln Met Ala Pro Ala Val Ser Lys Thr Glu Asp
            2645                    2650                    2655

Val Trp Val Arg Ile Glu Asp Cys Pro Ile Asn Asn Pro Arg Ser Gly
            2660                    2665                    2670

Arg Ser Pro Thr Gly Asn Thr Pro Pro Val Ile Asp Ser Val Ser Glu
            2675                    2680                    2685

Lys Ala Asn Pro Asn Ile Lys Asp Ser Lys Asp Asn Gln Ala Lys Gln
            2690                    2695                    2700

Asn Val Gly Asn Gly Ser Val Pro Met Arg Thr Val Gly Leu Glu Asn
2705                    2710                    2715                    2720

Arg Leu Asn Ser Phe Ile Gln Val Asp Ala Pro Asp Gln Lys Gly Thr
            2725                    2730                    2735

Glu Ile Lys Pro Gly Gln Asn Asn Pro Val Pro Val Ser Glu Thr Asn
            2740                    2745                    2750

Glu Ser Ser Ile Val Glu Arg Thr Pro Phe Ser Ser Ser Ser Ser Ser
            2755                    2760                    2765

Lys His Ser Ser Pro Ser Gly Thr Val Ala Ala Arg Val Thr Pro Phe
            2770                    2775                    2780

Asn Tyr Asn Pro Ser Pro Arg Lys Ser Ser Ala Asp Ser Thr Ser Ala
2785                    2790                    2795                    2800

Arg Pro Ser Gln Ile Pro Thr Pro Val Asn Asn Asn Thr Lys Lys Arg
            2805                    2810                    2815

Asp Ser Lys Thr Asp Ser Thr Glu Ser Ser Gly Thr Gln Ser Pro Lys
            2820                    2825                    2830

Arg His Ser Gly Ser Tyr Leu Val Thr Ser Val Lys Arg Gly Arg Met
            2835                    2840                    2845

Lys Leu Arg Lys Phe Tyr Val Asn Tyr Asn Cys Tyr Ile Asp Ile Leu
            2850                    2855                    2860

Phe Gln Met Lys Leu Lys Thr Glu Lys Phe Cys Lys Val Phe Leu Leu
2865                    2870                    2875                    2880

Glu Gly Phe Cys Ser Gly Ser His Ile Tyr Thr Leu Ser Ser Leu Val
            2885                    2890                    2895

Leu Phe Trp Glu Ala Leu Leu Met Val Arg Lys Lys Ile Val Lys Pro
            2900                    2905                    2910

Ser Met Phe Val Gln Tyr Val Leu His Val Phe Lys Val Ala Pro Ile
            2915                    2920                    2925

Pro Thr Ser Phe Asn Tyr Cys Leu Ser Asn Asn Glu His Tyr Arg Lys
            2930                    2935                    2940

Ile Tyr Ile Ala Val Ile Asn His Phe Ile Ile Asn Leu Asn Leu His
2945                    2950                    2955                    2960

Gln Gly Lys Ile Gly Ile Tyr Ala Lys Lys Asn Val Phe
            2965                    2970

( 2 ) INFORMATION FOR SEQ ID NO:8:

( i ) SEQUENCE CHARACTERISTICS:

(A) LENGTH: 486 amino acids
(B) TYPE: amino acid
(C) STRANDEDNESS: single
(D) TOPOLOGY: linear (ii) MOLECULE TYPE: None (xi) SEQUENCE DESCRIPTION: SEQ ID NO:8:

```
Met Pro Gln Leu Asp Ser Gly Gly Gly Ala Gly Gly Gly Asp Asp
 1               5                  10                  15

Leu Gly Ala Pro Asp Glu Leu Leu Ala Phe Gln Asp Glu Gly Glu Glu
            20                  25                  30

Gln Asp Asp Lys Ser Arg Asp Ser Ala Gly Pro Glu Arg Asp Leu Ala
                35                  40                  45

Glu Leu Lys Ser Ser Leu Val Asn Glu Ser Glu Gly Ala Ala Gly Ser
        50                  55                  60

Ala Gly Ile Pro Gly Val Pro Gly Ala Gly Ala Gly Ala Arg Gly Glu
 65                  70                  75                  80

Ala Glu Ala Leu Gly Arg Glu His Arg Ala Gln Arg Leu Phe Pro Asp
                85                  90                  95

Lys Leu Pro Glu Pro Leu Glu Asp Gly Leu Lys Ala Pro Glu Cys Thr
                100                 105                 110

Ser Gly Met Tyr Lys Glu Thr Val Tyr Ser Ala Phe Asn Leu Leu Met
            115                 120                 125

His Tyr Pro Pro Pro Ser Gly Ala Gly Gln His Pro Gln Pro Gln Pro
    130                 135                 140

Pro Leu His Lys Ala Asn Gln Pro Pro His Gly Val Pro Gln Leu Ser
145                 150                 155                 160

Leu Tyr Glu His Phe Asn Ser Pro His Pro Thr Pro Ala Pro Ala Asp
                165                 170                 175

Ile Ser Gln Lys Gln Val His Arg Pro Leu Gln Thr Pro Asp Leu Ser
                180                 185                 190

Gly Phe Tyr Ser Leu Thr Ser Gly Ser Met Gly Gln Leu Pro His Thr
            195                 200                 205

Val Ser Trp Pro Ser Pro Pro Leu Tyr Pro Leu Ser Pro Ser Cys Gly
    210                 215                 220

Tyr Arg Gln His Phe Pro Ala Pro Thr Ala Ala Pro Gly Ala Pro Tyr
225                 230                 235                 240

Pro Arg Phe Thr His Pro Ser Leu Met Leu Gly Ser Gly Val Pro Gly
                245                 250                 255

His Pro Ala Ala Ile Pro His Pro Ala Ile Val Pro Pro Ser Gly Lys
            260                 265                 270

Gln Glu Leu Gln Pro Phe Asp Arg Asn Leu Lys Thr Gln Ala Glu Ser
            275                 280                 285

Lys Ala Glu Lys Glu Ala Lys Lys Pro Thr Ile Lys Lys Pro Leu Asn
    290                 295                 300

Ala Phe Met Leu Tyr Met Lys Glu Met Arg Ala Lys Val Ile Ala Glu
305                 310                 315                 320

Cys Thr Leu Lys Glu Ser Ala Ala Ile Asn Gln Ile Leu Gly Arg Arg
                325                 330                 335

Trp His Ala Leu Ser Arg Glu Glu Gln Ala Lys Tyr Tyr Glu Leu Ala
            340                 345                 350

Arg Lys Glu Arg Gln Leu His Met Gln Leu Tyr Pro Gly Trp Ser Ala
                355                 360                 365

Arg Asp Asn Tyr Gly Lys Lys Lys Arg Arg Ser Arg Glu Lys His Gln
    370                 375                 380
```

| | | | | | | | | | | | | | | |
|---|---|---|---|---|---|---|---|---|---|---|---|---|---|---|
| Glu<br>385 | Ser | Thr | Thr | Gly | Gly<br>390 | Lys | Arg | Asn | Ala | Phe<br>395 | Gly | Thr | Tyr | Pro | Glu<br>400 |
| Lys | Ala | Ala | Ala | Pro<br>405 | Ala | Pro | Phe | Leu | Pro<br>410 | Met | Thr | Val | Leu | Ala<br>415 | Ala |
| Pro | Gly | Pro | Gln<br>420 | Leu | Pro | Arg | Thr | His<br>425 | Pro | His | Thr | Ile | Cys<br>430 | Cys | Pro |
| Ala | Ser | Pro<br>435 | Gln | Asn | Cys | Leu | Leu<br>440 | Ala | Leu | Arg | Ser | Arg<br>445 | His | Leu | His |
| Pro | Gln<br>450 | Val | Ser | Pro | Leu | Leu<br>455 | Ser | Ala | Ser | Gln | Pro<br>460 | Gln | Gly | Pro | His |
| Arg<br>465 | Pro | Pro | Ala | Ala | Pro<br>470 | Cys | Arg | Ala | His | Arg<br>475 | Tyr | Ser | Asn | Arg | Asn<br>480 |
| Leu | Arg | Asp | Arg | Trp | Pro<br>485 | | | | | | | | | | |

(2) INFORMATION FOR SEQ ID NO:9:

(i) SEQUENCE CHARACTERISTICS:
        (A) LENGTH: 511 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:9:

| | | | | | | | | | | | | | | | |
|---|---|---|---|---|---|---|---|---|---|---|---|---|---|---|---|
| Met<br>1 | Pro | Gln | Leu | Asp<br>5 | Ser | Gly | Gly | Gly | Ala<br>10 | Gly | Gly | Gly | Asp | Asp<br>15 | |
| Leu | Gly | Ala | Pro<br>20 | Asp | Glu | Leu | Leu | Ala<br>25 | Phe | Gln | Asp | Glu | Gly<br>30 | Glu | Glu |
| Gln | Asp | Asp<br>35 | Lys | Ser | Arg | Asp | Ser<br>40 | Ala | Gly | Pro | Glu | Arg<br>45 | Asp | Leu | Ala |
| Glu | Leu<br>50 | Lys | Ser | Ser | Leu | Val<br>55 | Asn | Glu | Ser | Glu | Gly<br>60 | Ala | Ala | Gly | Ser |
| Ala<br>65 | Gly | Ile | Pro | Gly | Val<br>70 | Pro | Gly | Ala | Gly | Ala<br>75 | Gly | Ala | Arg | Gly | Glu<br>80 |
| Ala | Glu | Ala | Leu | Gly<br>85 | Arg | Glu | His | Arg | Ala<br>90 | Gln | Arg | Leu | Phe | Pro<br>95 | Asp |
| Lys | Leu | Pro | Glu<br>100 | Pro | Leu | Glu | Asp | Gly<br>105 | Leu | Lys | Ala | Pro | Glu<br>110 | Cys | Thr |
| Ser | Gly | Met | Tyr<br>115 | Lys | Glu | Thr | Val<br>120 | Tyr | Ser | Ala | Phe | Asn<br>125 | Leu | Leu | Met |
| His | Tyr | Pro<br>130 | Pro | Pro | Ser | Gly | Ala<br>135 | Gly | Gln | His | Pro | Gln<br>140 | Pro | Gln | Pro |
| Pro | Leu<br>145 | His | Lys | Ala | Asn | Gln<br>150 | Pro | Pro | His | Gly<br>155 | Val | Pro | Gln | Leu | Ser<br>160 |
| Leu | Tyr | Glu | His | Phe<br>165 | Asn | Ser | Pro | His<br>170 | Pro | Thr | Pro | Ala | Pro<br>175 | Ala | Asp |
| Ile | Ser | Gln | Lys<br>180 | Gln | Val | His | Arg<br>185 | Pro | Leu | Gln | Thr | Pro<br>190 | Asp | Leu | Ser |
| Gly | Phe | Tyr<br>195 | Ser | Leu | Thr | Ser | Gly<br>200 | Ser | Met | Gly | Gln | Leu<br>205 | Pro | His | Thr |
| Val | Ser<br>210 | Trp | Pro | Ser | Pro | Pro<br>215 | Leu | Tyr | Pro | Leu | Ser<br>220 | Pro | Ser | Cys | Gly |
| Tyr<br>225 | Arg | Gln | His | Phe | Pro<br>230 | Ala | Pro | Thr | Ala | Ala<br>235 | Pro | Gly | Ala | Pro | Tyr<br>240 |

| | | | | | | | | | | | | | | | |
|---|---|---|---|---|---|---|---|---|---|---|---|---|---|---|---|
|Pro|Arg|Phe|Thr|His<br>245|Pro|Ser|Leu|Met|Leu<br>250|Gly|Ser|Gly|Val|Pro<br>255|Gly|
|His|Pro|Ala|Ala<br>260|Ile|Pro|His|Pro|Ala<br>265|Ile|Val|Pro|Pro|Ser<br>270|Gly|Lys|
|Gln|Glu|Leu<br>275|Gln|Pro|Phe|Asp|Arg<br>280|Asn|Leu|Lys|Thr|Gln<br>285|Ala|Glu|Ser|
|Lys|Ala<br>290|Glu|Lys|Glu|Ala|Lys<br>295|Lys|Pro|Thr|Ile|Lys<br>300|Lys|Pro|Leu|Asn|
|Ala<br>305|Phe|Met|Leu|Tyr|Met<br>310|Lys|Glu|Met|Arg|Ala<br>315|Lys|Val|Ile|Ala|Glu<br>320|
|Cys|Thr|Leu|Lys|Glu<br>325|Ser|Ala|Ala|Ile|Asn<br>330|Gln|Ile|Leu|Gly|Arg<br>335|Arg|
|Trp|His|Ala|Leu<br>340|Ser|Arg|Glu|Glu|Gln<br>345|Ala|Lys|Tyr|Tyr|Glu<br>350|Leu|Ala|
|Arg|Lys|Glu<br>355|Arg|Gln|Leu|His|Met<br>360|Gln|Leu|Tyr|Pro|Gly<br>365|Trp|Ser|Ala|
|Arg|Asp<br>370|Asn|Tyr|Gly|Lys|Lys<br>375|Lys|Arg|Arg|Ser|Arg<br>380|Glu|Lys|His|Gln|
|Glu<br>385|Ser|Thr|Thr|Asp|Pro<br>390|Gly|Ser|Pro|Lys|Lys<br>395|Cys|Arg|Ala|Arg|Phe<br>400|
|Gly|Leu|Asn|Gln|Gln<br>405|Thr|Asp|Trp|Cys|Gly<br>410|Pro|Cys|Arg|Arg|Lys<br>415|Lys|
|Lys|Cys|Ile|Arg<br>420|Tyr|Leu|Pro|Gly|Glu<br>425|Gly|Arg|Cys|Pro|Ser<br>430|Pro|Val|
|Pro|Ser|Asp<br>435|Asp|Ser|Ala|Leu|Gly<br>440|Cys|Pro|Gly|Ser|Pro<br>445|Ala|Pro|Gln|
|Asp|Ser<br>450|Pro|Ser|Tyr|His|Leu<br>455|Leu|Pro|Arg|Phe|Pro<br>460|Thr|Glu|Leu|Leu|
|Thr<br>465|Ser|Pro|Ala|Glu|Pro<br>470|Ala|Pro|Thr|Ser|Pro<br>475|Gly|Leu|Ser|Thr|Ala<br>480|
|Leu|Ser|Leu|Pro|Thr<br>485|Pro|Gly|Pro|Pro|Gln<br>490|Ala|Pro|Arg|Ser|Thr<br>495|Leu|
|Gln|Ser|Thr|Gln<br>500|Val|Gln|Gln|Gln|Glu<br>505|Ser|Gln|Arg|Gln|Val<br>510|Ala| |

( 2 ) INFORMATION FOR SEQ ID NO:10:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:10:

| | | | | | | | | | | | | | | | |
|---|---|---|---|---|---|---|---|---|---|---|---|---|---|---|---|
|Ser<br>1|Tyr|Leu|Asp|Ser<br>5|Gly|Ile|His|Ser|Gly<br>10|Ala|Thr|Thr|Ala|Pro<br>15|Ser|
|Leu|Ser|Gly<br>20| | | | | | | | | | | | | |

( 2 ) INFORMATION FOR SEQ ID NO:11:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:11:

Ser Tyr Leu Gly Asp Ser Gly Ile His Ser Gly Ala Val Thr Gln Val
1               5                   10                  15

Pro Ser Leu Ser Gly
            20